US007141573B2

(12) United States Patent
Hanson et al.

(10) Patent No.: US 7,141,573 B2
(45) Date of Patent: Nov. 28, 2006

(54) POLYPHARMACOPHORIC AGENTS

(75) Inventors: Robert N. Hanson, Newton, MA (US); John W. Babich, Scituate, MA (US)

(73) Assignee: Molecular Insight Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 09/758,957

(22) Filed: Jan. 11, 2001

(65) Prior Publication Data

US 2002/0042357 A1    Apr. 11, 2002

Related U.S. Application Data

(60) Provisional application No. 60/175,617, filed on Jan. 11, 2000.

(51) Int. Cl.
 *A61K 31/497* (2006.01)
 *C07D 211/00* (2006.01)
(52) U.S. Cl. ............................. 514/252.12; 514/255.04; 546/184; 546/205; 546/239; 568/659; 562/405; 562/468; 544/358; 544/396
(58) Field of Classification Search ................ 435/7.1, 435/7.2; 436/501, 518; 562/405; 568/303; 544/358, 392–394, 397; 514/252.12, 252
See application file for complete search history.

(56) References Cited

U.S. PATENT DOCUMENTS

| 4,202,896 | A | * | 5/1980 | Gootjes | ...................... 424/250 |
| 4,265,894 | A | * | 5/1981 | Gootjes | ...................... 424/250 |
| 4,634,792 | A |   | 1/1987 | Zanno et al. | ............... 560/169 |
| 5,208,260 | A |   | 5/1993 | Cordi et al. | ................ 514/561 |
| 5,369,113 | A | * | 11/1994 | Moldt et al. | ................ 514/304 |
| 5,733,756 | A | * | 3/1998 | Zeitlin et al. | ............... 435/122 |

FOREIGN PATENT DOCUMENTS

| EP | 0 263 502 A2 | 4/1988 |
| EP | 0 315 519 A2 | 5/1989 |
| EP | 0 417 803 A1 | 3/1991 |
| WO | WO 98/00398 | 1/1998 |
| WO | WO 99/61055 | 12/1999 |

OTHER PUBLICATIONS

Solomons, T. W. G. Organic Chemistry Fifth Edition. New York: John Wiley and Sons. 1992, pp. 796-797.*
Silverman, R. B. The Organic Chemistry of Drug Design and Drug Action. New York: Academic Press, Inc. 1992.*
Dutta, A. K.; Coffey, L. L.; Reith, M. E. A. "Potent and Selective Ligands for the Dopamine Transporter (DAT): Structure-Activity Relationship Studies of Novel 4-[2-(Diphenylmethoxy)ethyl]-1-(3-phenylpropyl)piperidine Analogues" J. Med. Chem. 1998, 41, 699.*
Mewshaw et al.; "New Generation Dopaminergic Agents 1. Discovery of a Novel Scaffold Which Embraces the $D_2$ Agonist Pharmacophore. Structure- Activity Relationships of a Series of 2-(Aminomethyl ) Chromans", J. Med. Chem. 40: 4235-4256, (1997).
Jacoby et al.; "A Structural Rationale for the Design of Water Soluble Peptide-Derived Neurokinin-1 Antagonists", J. Recept. Signal Transduction Res. 17(6):855-873, (1997).
International Search Report Completed on Jul. 25, 2001, and mailed on Aug. 8, 2001.

* cited by examiner

*Primary Examiner*—Jon Epperson
(74) *Attorney, Agent, or Firm*—Foley & Lardner LLP; Michel Morency; James F. Ewing

(57) ABSTRACT

One aspect of the present invention relates to polypharmacophoric compounds. In certain embodiments, the polyphamacophore compounds comprise individual pharmacophore units selected from the group consisting of D-1 agonists, D-2 agonists, D-3 agonists, D-4 agonists, irreversible monoamine inhibitors, reversible monoamine inhibitors, monoamine transporter inhibitors, COMT inhibitors, MAO inhibitors, and dopamine transporter inhibitors. Moreover, the present invention also relates to combinatorial libraries of polypharmacophoric compounds. Another aspect of the present invention relates to the use of a polypharmacophoric compound in a method of treating a mammal in need thereof. For example, a polypharmacophoric compound of the present invention may be used in a method of treating a mammal afflicted with Alzheimer's Disease, Huntington's Disease, depression, attention deficit disorder, autism, obesity, or inflammation.

3 Claims, 17 Drawing Sheets traditional hybrid drug  novel scaffolded polypharmacophore

GBR 12935

ZHN-94

ZHN-92

ZHN-93

Z-24

Z-26(48)

Z-28

Z-39

Z-31

Z-44

Z-52

Z-59

Z-58

POLYPHARMACOPHORIC AGENTS

RELATED APPLICATIONS

This application claims the benefit of priority to U.S. Provisional Patent Application Ser. No. 60/175,617, filed Jan. 11, 2000.

BACKGROUND OF THE INVENTION

The degeneration of 50–70% of the population of dopaminergic neurons in the human brain results in the profound disturbances of motor function that are characteristic of Parkinson's Disease (PD). As this degeneration of neurons progresses, the symptoms become increasingly severe, leading not only to loss of motor function but also to an increased incidence of dementia and other neurological disorders. Currently, over a million people in North America are affected by this disease whose single most consistent risk factor is age. Because the population of the elderly is expected to increase over the next four decades, it is projected that neurodegenerative diseases, such as Parkinson's Disease, may pass cancer as the second most common cause of death among the elderly. Therefore, the development of therapeutic agents that can delay the onset of disease, slow its progression, or enhance the effectiveness of other drugs, will provide a substantial contribution to reducing the mortality and morbidity due to Parkinson's Disease among the elderly and increasing the quality of life for afflicted individuals.

Treatment of Parkinson's Disease has traditionally been subdivided into three categories: preventive, symptomatic and restorative intervention. The latter intervention, which include transplantation of adrenal medulla cells, intraventricular delivery of dopaminergic neurotrophic factor GDNF, and gene therapy, are in very early stages of safety and efficacy trials. Protective therapy with selective monoamine oxidase B (MAO-B) inhibitors, such as selegiline, has been unproductive to date. Early trials, which indicated promise, could largely be explained through amelioration of symptoms rather than by slowing the progression of the disease. As a result, most of the current efforts continue to focus on therapeutic agents that affect symptoms which accompany the disease rather than to reverse or prevent it. This remains an important area for medical research, due to the problems that exist with current therapeutic interventions.

Evaluation of the literature indicates that levodopa (L-DOPA) still remains the agent of choice for the initial treatment of PD. There is clearly a beneficial motor response to this drug during the early states of the disease, however, as the disease progresses, the effectiveness of the drug is reduced and other side effects become more pronounced. Patients may experiece fluctuations in motor response, dyskineasias, or psychiatric disturbances, such as nightmares, hallucinations, psychosis or depression. Alternatives, for example, the use of amantidine, selegiline or anti-cholinergic agents may provide some initial benefit, but in most cases patients still require levodopa or other dopamine (DA) agonists for effective symptomatic relief. Even the DA agonists, when used as monotherapeutic agents, often fail to exceed the effectiveness of levodopa.

The declining efficacy of the major therapeutic agents and the appearance of other manifestations during the course of the disease suggest additional therapeutic strategies. Among the proposed directions are new formulations of levodopa to improve the delivery of the drug to the affected region of the brain, selective serotonin reuptake inhibitors (SSRI's) and monoamine oxidase inhibitors (MAO I) to treat depression in PD patients, dopamine transporter (DAT), and catechol O-methyl transferase (COMT) inhibitors to prolong the effects of DA, and DA receptor (D1) agonists to reduce dyskinesias. All of these approaches utilize separate discrete molecular entities to elicit the desired response, either alone or in combination with other agents. As such, they are subject to limitations often associated with combination therapy, for example, noncompliance due to different dosing schedules and drug-drug interactions.

As shown in FIG. 1, which depicts a model dopaminergic neuron, in addition to having the processes for dopamine synthesis, this region contains the dopamine transporter (DAT) which is responsible for removal of dopamine from the synapse, catechol O-methyl transferase (COMT) and monoamine oxidases (MAO-A and B) which are involved in DA metabolism, and DA receptors (D1, D2, D2, etc.) which mediate dopaminergic responses. Thus, intervention at one site alone or selectively, as is the common for traditional therapeutics, may only produce a partial response because of compensatory mechanisms mediated by the other sites. Because of this decreased response, often a greater dose must be utilized which often results in adverse side effects. In contrast, an intervention strategy which affects several sites at a dose level that may be ineffective if present solely, may produce an additive response that would be therapeutically beneficial, while reducing the possibility for adverse side effects. Although FIG. 1 depicts the dopaminergic neuron, it will be appreciated that other regions having multiple receptor sites in close proximity may be involved in other diseases and conditions, and thus also may utilize this intervention strategy.

Clearly, because of the need to increase the efficacy and safety of pharmaceuticals, it would be beneficial to develop pharmaceuticals which contain multiple pharmacophoric sites capable of interacting at multiple biological sites, preferably for those biological sites which act in concert, implicated in specific diseases and conditions and/or involved in side effects of these diseases or conditions.

SUMMARY OF THE INVENTION

Figure 1:
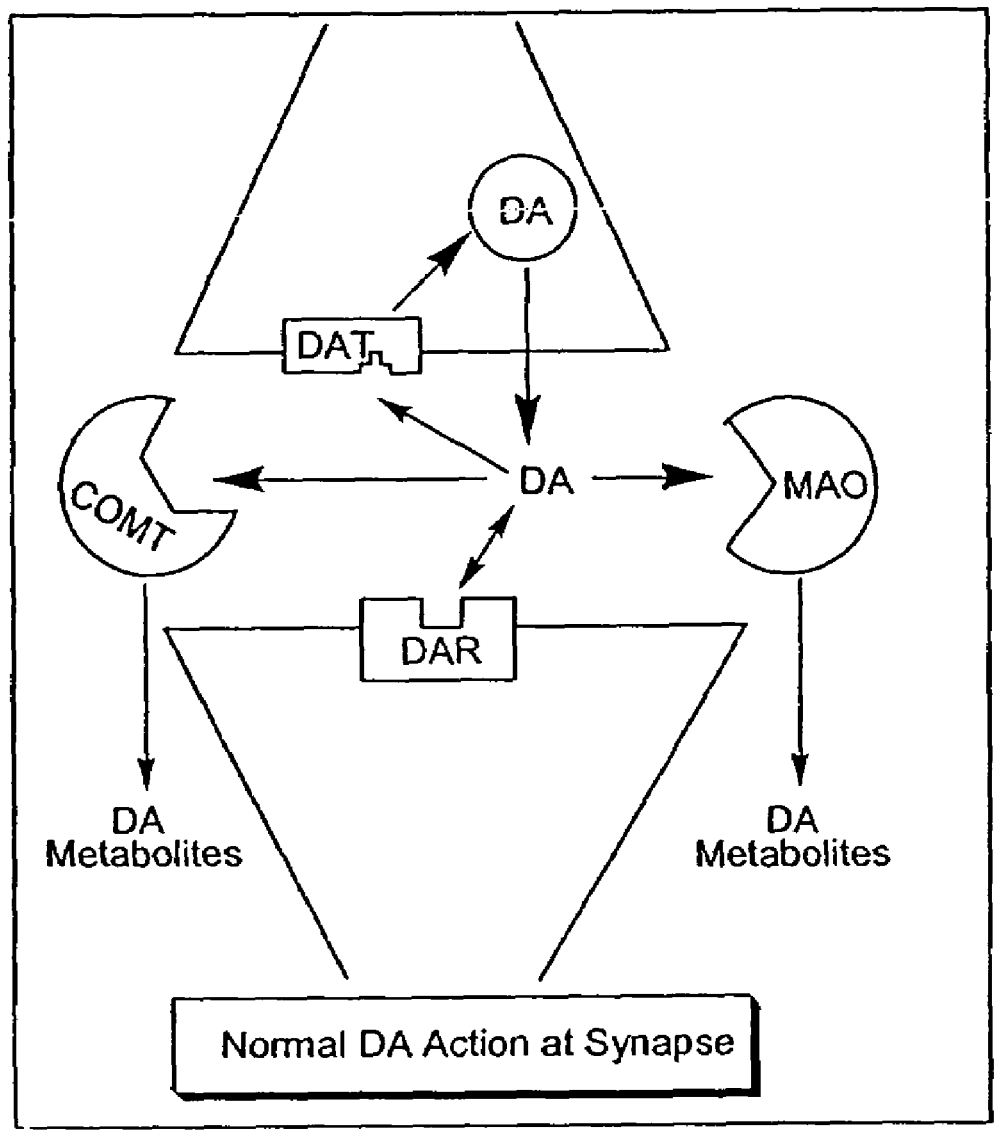
FIG. 1 depicts a model dopaminergic neuron.

The present invention recognizes that it is often desirable, in the treatment, prevention, and diagnosis of a disease or condition, to utilize an agent that is able to interact at more than one biological site. For example, this may include, but is not limited to, eliciting or inhibiting a biological response for a condition that implicates more than one receptor site, preferably for those biological receptor sites that act in concert, or eliciting or inhibiting biological responses, in addition to those involved in the particular condition, to treat side effects. Thus, in recognition of the need for, and the desirability of this approach, in one aspect, the present invention provides novel polypharmacophoric scaffolds, libraries thereof, and methods for making said scaffolds and libraries thereof.

In general, the polypharmacophoric scaffolds comprise a scaffold unit having at least two pharmacophoric units appended thereto, whereby each is capable of interacting at a biological site and/or eliciting or inhibiting a desired biological response. In certain preferred embodiments, the pharmacophoric units are selected for their ability to elicit a response at two or more biological receptor sites that preferably act in concert and optionally are either physically or spatially close (e.g., DA agonist and DAT receptors) or can be functionally connected (for example, via the polypharmacophoric unit). In certain embodiments, the scaffold units and/or the pharmacophoric units have one or more modifier units attached thereto, whereby these modifier units are selected to facilitate the delivery, synthesis, activation, absorption, solubility or detection (e.g., by the use of fluorescent or radioactive moieties, or biotin, to name a few) of the scaffold pharmacophoric units.

The novel scaffolded polypharmacophores can be depicted generally by formulas (I) and (IA):

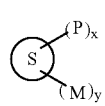

(I)

As depicted in formula (I), S comprises a scaffold unit; P comprises a pharmacophore, wherein x is greater than or equal to 2; M comprises a modifier unit, wherein y is greater than or equal to 0, whereby each one of P and M, for each occurrence, is appended to said scaffold unit and said scaffold unit does not participate directly in the desired pharmacological activity. In addition to modifier units being directly appended to the scaffold, in certain other embodiments, as shown in (IA), additional modifier units (D), wherein a and b, for each occurrence of x or y, are each independently greater than or equal to zero, may also be directly attached to one or more pharmacophores (P) and/or to one or more existing modifier units (M) that are attached to the scaffold.

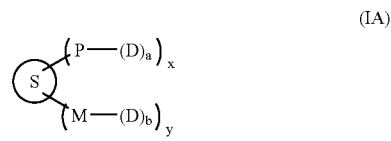

(IA)

In certain embodiments, each additional modifier unit can be linked sequentially to either an existing modifier, M, or to a pharmacophore, P, to generate either of the appendages: S-M-$D_1$-$D_2$-$D_3$ (etc.) or S-P-$D_1$-$D_2$-$D_3$ (etc.). In certain other embodiments, each additional modifier can be linked directly to the pharmacophore (P) or modifier unit (M) to generate either of the appendages:

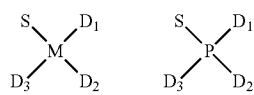

In still other embodiments, each additional modifier can, in certain instances, be linked directly to the pharmacophore or modifier unit, and in other instances also be linked sequentially to generate combinations of appendages as shown for certain exemplary appendages below:

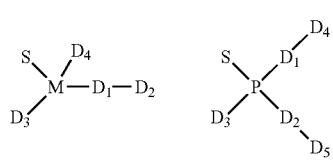

In a preferred embodiment, the scaffolded polypharmacophores, as depicted in (I) and (IA), are utilized in diseases and/or conditions that implicate the dopaminergic neuron, and that include two or more signalling pathways and/or modulators thereof. Thus, the inventive polypharmacophores can be utilized to treat any neurological disorder. In particularly preferred embodiments, the pharmacophores utilized in the present invention are selected to interact at a biological site in the region of the dopaminergic neuron, wherein each of said pharmacophores are preferably independently selected from the group consisting of D-1 agonist, D-2 agonist, D-3 agonist, D-4 agonist, irreversible MAO-inhibitors, reversible MAO-inhibitors, monoamine transporter inhibitors, COMT-inhibitors, MAO-inhibitors, DA transporter inhibitors, 5HT inhibitors, NET inhibitors, and GABA inhibitors. It is also particularly preferred that the scaffolded polypharmacophore comprises two, and more preferably three, pharmacophores.

In other embodiments of the present invention, polypharmacophoric scaffolds and libraries thereof are provided as shown in Formulas (II) and (IIA).

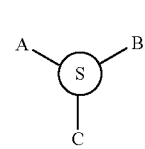

(II)

-continued

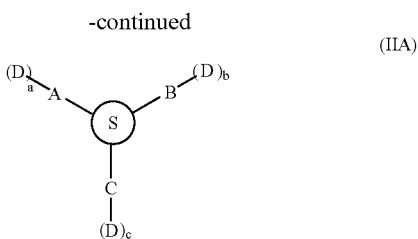
(IIA)

As shown in Formula (II), at least two of A, B, or C comprise a pharmacophore. In certain preferred embodiments, A, B, and C each comprise a pharmacophore. In other preferred embodiments, at least two of A, B, or C comprise a pharmacophore and one of A, B, or C comprises a modifier unit. As shown in Formula (IIA), in certain other preferred embodiments, one or more additional modifier units may also be attached one or more of A, B, or C. As discussed in more detail above for Formula (I), modifiers may be attached sequentially to one or more of A, B, or C; modifiers may each be directly attached to one or more of A, B, or C; or modifiers may be attached both sequentially and directly to one or more of A, B, or C. In particularly preferred embodiments, the pharmacophores utilized in the present invention are selected to interact at a biological site in the region of the dopaminergic neuron, wherein each of said pharmacophores are preferably independently selected from the group consisting of D-1 agonist, D-2 agonist, D-3 agonist, D-4 agonist, irreversible MAO-inhibitors, reversible MAO-inhibitors, monoamine transporter inhibitors, COMT-inhibitors, MAO-inhibitors, and DA transporter inhibitors.

In another exemplary embodiment of the present invention, polypharmacophoric scaffolds and libraries thereof are provided as shown in formulas (III) and (IIIA):

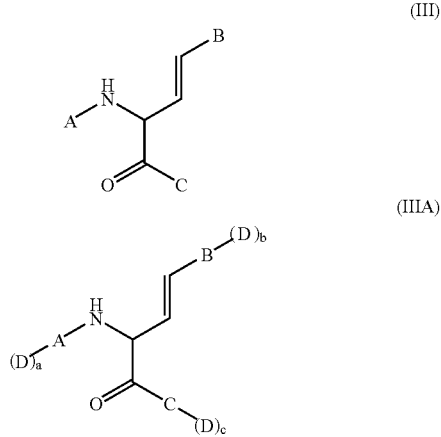

wherein A, B, and C each comprise a desired pharmacophore or modifier unit. It is particularly preferred that two of A, B, or C comprises a pharmacophore and one of A, B, or C comprises a modifier unit. As shown in (IIIA), each of A, B, or C may also have one or more additional modifier units, D, attached thereto. As discussed in more detail above for Formula (I), modifiers may be attached sequentially to one or more of A, B, or C; modifiers may each be directly attached to one or more of A, B, or C; or modifiers may be attached both sequentially and directly to one or more of A, B, or C. In particularly preferred embodiments, the pharmacophores utilized in the present invention are selected to interact at a biological site in the region of the dopaminergic neuron, wherein each of said pharmacophores are preferably independently selected from the group consisting of D-1 agonist, D-2 agonist, D-3 agonist, D-4 agonist, irreversible MAO-inhibitors, reversible MAO-inhibitors, monoamine transporter inhibitors, COMT-inhibitors, MAO-inhibitors, and DA transporter inhibitors.

The invention also provides a method for determining one or more biological activities of an inventive polypharmacophore or library of polypharmacophores comprising contacting a scaffolded polypharmacophore or library of scaffolded polypharmacophores having any one of formulas (I), (IA), (II), (IIA), (III), or (IIIA) to a biological target, and determining a statistically significant change in a biochemical activity relative to the level of biochemical activity in the absence of a scaffolded polypharmacophore.

In another aspect, the present invention also provides a pharmaceutical composition comprising a compound of any one of the formulas (I), (IA), (II), (IIA), or (IIIA) as described herein; or a pharmaceutically acceptable salt thereof; in combination with a pharmaceutically acceptable diluent or carrier.

In yet another aspect, the invention provides a method for the treatment of disorders and or conditions implicating multiple receptor sites (e.g., more than one), preferably those that act in concert, in an animal, comprising administering a pharmaceutically effective dose of a compound of any one of formulas (I), (IA), (II), (IIA), (III), or (IIIA), or a pharmaceutically acceptable salt thereof. In a particularly preferred embodiment, the present invention provides a method for the treatment of conditions in which the dopaminergic system is implicated, comprising administering a pharmaceutically effective dose of any one of compounds of formulas (I), (IA), (II), (IIA), (III), or (IIIA) or a pharmaceutically acceptable salt thereof. In preferred embodiments, the method is used to modulate the function of the dopaminergic system.

The invention also provides the use of a compound of any one of formulas (I), (IA), (II), (IIA), (III), or (IIIA); or a pharmaceutically acceptable salt thereof; to prepare a medicament useful for treating a condition which implicates biological systems which act in concert. In preferred embodiments, the medicament is used for treating a condition in which the dopaminergic system is implicated, and preferably the medicament is used to modulate the function of the dopaminergic system.

In yet another aspect, the present invention provides a composition comprising a compound of any one of formulas (I), (IA), (II), (IIA), (III), or (IIIA) or a pharmaceutically acceptable salt thereof, for use in medical therapy or diagnosis. In a preferred embodiment, the invention provides a labeled compound comprising a radionuclide, fluroescent tag or other label or identifier, and a compound of any one of formulas (I), (IA), (II), (IIA), (III), or (IIIA), wherein any one or more of the pharmacophoric units or modifier units are labeled, using radiolabels, fluroescence or otherwise; or a pharmaceutically acceptable salt thereof, as well as methods for using such labeled compounds as an imaging or diagnostic agent (e.g., to identify, or evaluate the function of, specific binding sites in a particular organ of interest).

DEFINITIONS

"Pharmacophore": The term "pharmacophore", as used herein, refers to an agent capable of having a biological effect.

"Modifier Unit": The term "modifier unit", as used herein, refers to any moiety or combination of moieites capable of facilitating the delivery, synthesis, activation, solubility or other desirable property of an inventive scaffolded polypharmacophore. Exemplary modifier units include, but are not limited to, spacers, scaffold assemblers, bioactivating groups, and targeting agents, to name a few.

"Linker unit": The term "linker unit", as used herein, refers to a molecule, or group of molecules, connecting a solid support and a combinatorial library member. The linker may be comprised of a single linking molecule, or may comprise a linking molecule and a spacer molecule.

"Identifier Tag": The term "identifier tag" as used herein, refers to a means for recording a step in a series of reactions used in the synthesis of a chemical library. For the purposes of this application, the terms encoded chemical library and tagged chemical library both refer to libraries containing a means for recording each step in the reaction sequence for the synthesis of the chemical library.

"Targeting Moiety": The term "targeting moiety", as used herein, refers to any molecular structure which assists one or more of the appended pharmacophores or modifier units in localizing to a particular targeting area, entering a target cell(s), and/or binding to a target receptor. For examples, lipids (including cationic, neutral, and steroidal lipids, virosomes, and liposomes), antibodies, lectins, ligands, sugars, steroids, hormones, nutrients and proteins can serve as targeting moieties.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formate, or a ketone), a thiocarbonyl (such as a thioester, a thioacetate, or a thioformate), an alkoxyl, a phosphoryl, a phosphonate, a phosphinate, anamino, an amido, an amidine, an imine, a cyano, a nitro, an azido, a sulfhydryl, an alkylthio, a sulfate, a sulfonate, sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like. The term "arylkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, as for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, a heterocyclyl, an aromatic or heteroaromatic moiety, —$CF_3$, —CN, or the like.

The terms "heterocyclyl" or "heterocyclic group" refer to 4- to 10-membered ringtructures, more preferably 4- to 7-membered rings, which ring structures include one to four heteroatoms. Heterocyclyl groups include, for example, pyrrolidine, oxolane, thiolane, imidazole, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, arnido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

It will be noted that the structure of some of the compounds of this invention includes asymmetric carbon atoms. It is to be understood accordingly that the isomers arising from such asymmetry are included within the scope of this invention. Such isomers are obtained in substantially pure form by classical separation techniques and by sterically controlled synthesis.

The phrase "protecting group" as used herein, refers to a chemical group that reacts reactions for which protection is desired, can be selectively removed from the particular functionality that it protects to yield the desired functionality, and is removable in good yield by reagents compatible with the other functional group(s) generated during the reactions. Examples of such protecting groups include esters of carboxylic acids, ethers of alcohols and acetals and ketals of aldehydes and ketones.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The term "solid support" refers to a material having a rigid or semi-rigid surface. Such materials will preferably take the form of small beads, pellets, disks, chips, dishes, multi-well plates, wafers or the like, although other forms may be used. In some embodiments, at least one surface of the substrate will be substantially flat. The term "surface" refers to any generally two-dimensional structure on a solid substrate and may have steps, ridges, kinks, terraces, and the like without ceasing to be a surface.

The term "polymeric support", as used herein, refers to a soluble or insoluble polymer to which an amino acid or other chemical moiety can be covalently bonded by reaction with a functional group of the polymeric support. Many suitable polymeric supports are known, and include soluble polymers such as polyethylene glycols or polyvinyl alcohols, as well as insoluble polymers such as polystyrene resins. A suitable polymeric support includes functional groups such as those described below. A polymeric support is termed "soluble" if a polymer, or a polymer-supported compound, is soluble under the conditions employed. However, in general, a soluble polymer can be rendered insoluble under defined conditions. Accordingly, a polymeric support can be soluble under certain conditions and insoluble under other conditions.

The phrase "therapeutically-effective amount" as used herein means that amount of a compound, material, or composition of the present invention which is effective for producing some desired therapeutic effect in at least a sub-population of cells in an animal and thereby blocking the biological consequences of that event in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, including but not limited to, a liquid or solid filler, diluent, excipient, solvent or encapsulating material, involved in carrying or transporting the subject scaffolded polypharmacophores from one organ, or portion of the body, to another organ, or portion of the body.

"Subject": The term "subject", as used herein, refers to a human or animal (e.g., rat, mouse, cow, pig, horse, sheep, monkey, cat, dog, goat, etc.)

"Amino acid" or "amino acid residue" refers to any of the naturally occurring amino acids, as well as synthetic analogs and derivatives thereof. In general the abbreviations used herein for designating the amino acids and the protective groups are based on recommendations of the IUPAC-IUB Commission on Biochemical Nomenclature (see Biochemistry (1972) 11:1726–1732). "Amino acid" refers to any of the naturally occurring amino acids, as well as synthetic analogs and derivatives thereof. .alpha.-Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). See, e.g., Harper et al (1977) Review of Physiological Chemistry, 16th Ed., Lange Medical Publications, pp. 21–24. One of skill in the art will appreciate that the term "amino acid" also includes .beta.-, .gamma.-, .delta.-, and .omega.-amino acids, and the like. As used herein, the twenty conventional amino acids and their abbreviations follow conventional usage (see IMMUNOLOGY-A SYNTHESIS, 2nd Edition, E. S. Golub and D. R. Gren, Eds., Sinauer Associates, Sunderland, Mass. (1991), which is incorporated herein by reference). Amino acid residues are abbreviated as follows: Phenylalanine is Phe or F; Leucine is Leu or L; Isoleucine is Ile or I; Methionine is Met or M; Norleucine is Nle; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid.

The term "amino acid" or "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

It will also be appreciated that unnatural amino acids are within the scope of the present invention, as set forth in, for example, Williams (ed.), Synthesis of Optically Active alpha.-Amino Acids, Pergamon Press (1989); Evans et al., J. Amer. Chem. Soc., 112:4011–4030 (1990); Pu et al., J. Amer. Chem. Soc., 56:1280–1283 (1991); Williams et al., J. Amer. Chem. Soc., 113:9276–9286 (1991); and all references cited therein. Examples of unconventional amino acids include: 4-hydroxyproline, O-phosphoserine, N-acetylserine, N-formylmethionine, 3-methylhistidine, 5-hydroxylysine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Also included are the (D) and (L) stereoisomers of such amino acids, or unnatural amino acids, when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) or (L) stereoisomers. D- and L-α-Amino acids are represented by the following Fischer projections and wedge-and-dash drawings. In the majority of cases, D- and L-amino acids have R- and S-absolute configurations, respectively.

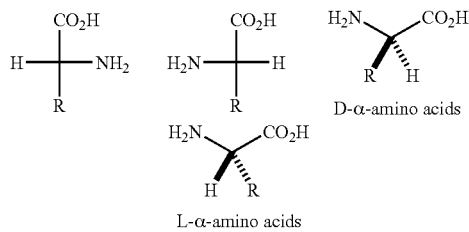

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g. the ability to bind to opioid receptors), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

DETAILED DESCRIPTION OF THE INVENTION

The present invention recognizes that it is often desirable, in the treatment, prevention, and diagnosis of a disease or condition, to utilize an agent that is able to interact at more than one biological site. For example, this may include, but is not limited to, eliciting or inhibiting a biological response for a condition that implicates more than one receptor site (preferably for biological sites capable of acting in concert), or eliciting or inhibiting biological responses, in addition to those involved in the particular condition, to treat side effects. Thus, in recognition of the need for, and the desirability of this approach, in one aspect, the present invention provides novel polypharmacophoric scaffolds, libraries thereof, and methods for making said scaffolds and libraries thereof.

Figure 2:
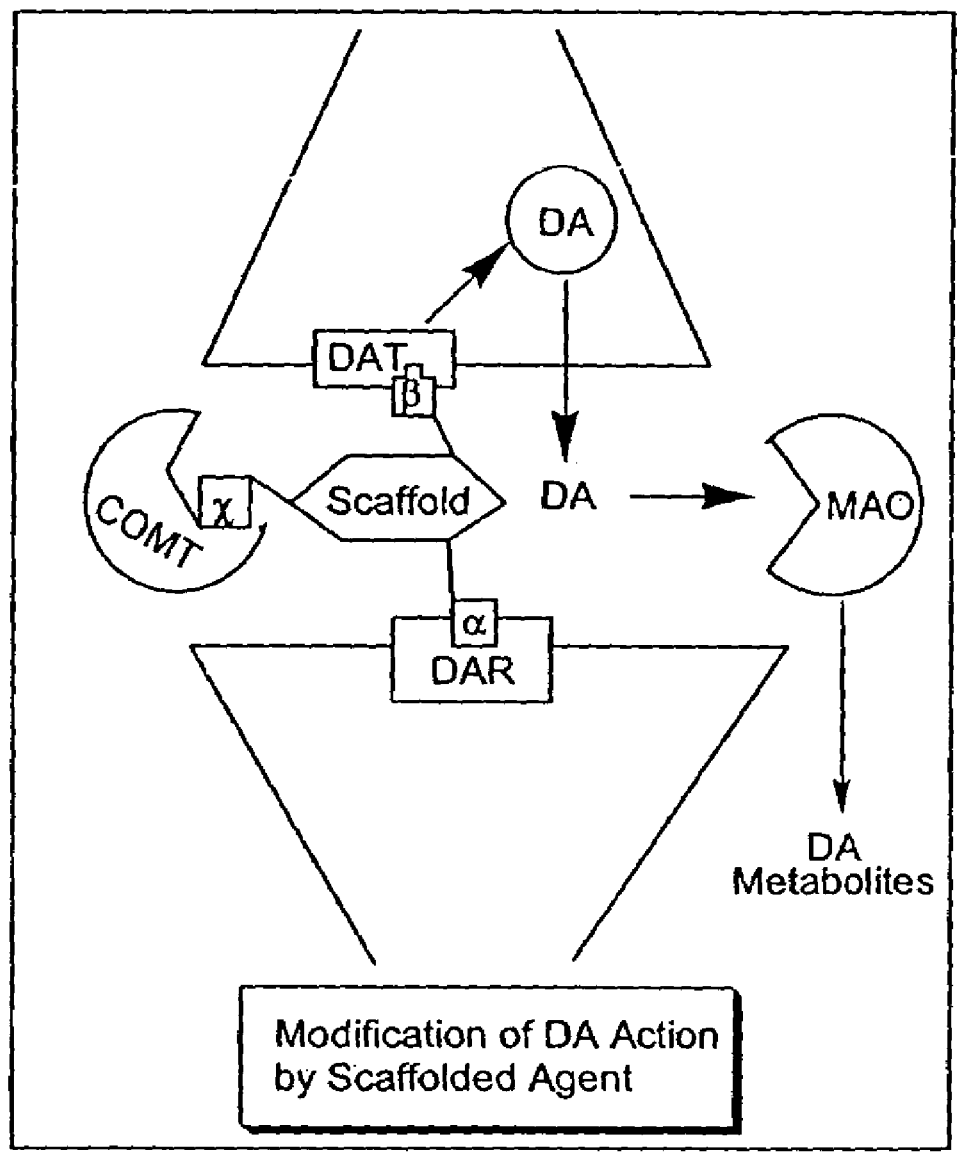
FIG. 2 depicts the modification of dopamine action by one embodiment of an inventive polypharmacophoric agent.

As described previously, currently utilized approaches to treatment of specific diseases or conditions generally involve the use of separate discrete molecular entities to elicit the desired response, either alone or in combination with other agents. In contrast to this traditional approach, FIG. 2 depicts the inventive approach to the development of therapeutics, in which a drug having multiple biological targets which act is concert, is capable of exerting multiple beneficial effects. For example, referring to FIG. 2, inhibition of DAT by pharmacophore component β would potentiate the effects of endogenous DA by preventing its reuptake. The binding of pharmacophore component α to the DA receptor (DAR) would supplement the effects of DA, and inhibition of COMT by pharmacophore component χ would retard the metabolism of endogenous DA. Because it would not be necessary to exert maximal effects at any one site, the likelihood of drug interactions or toxicity at other neuronal sites is reduced.

Figure 3:
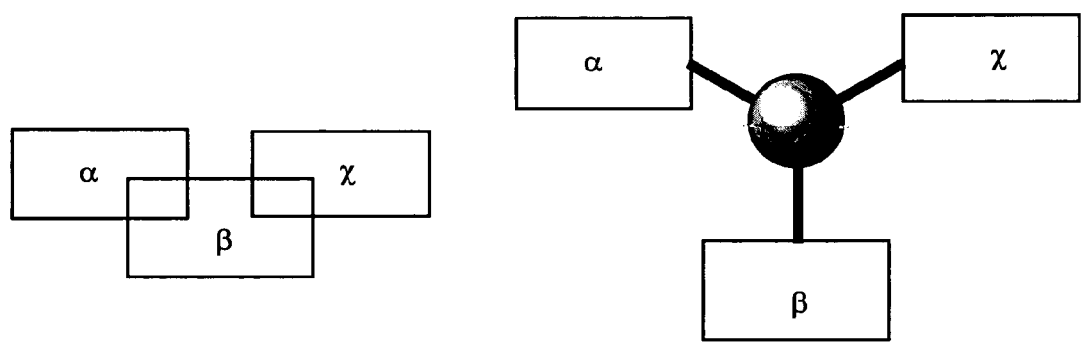
FIG. 3 depicts the contrast between hybrid drugs currently utilized and the inventive scaffolded polypharmacophores.

In general, the novel polypharmacophores of the present invention comprise a molecular scaffold, or "scaffold unit", as used herein, to which pharmacophoric groups associated with a particular therapy can be appended or inserted. These polypharmacophores preferably exert therapeutic effects for a particular condition in which multiple receptor sites involved in the condition are in close proximity. Because the novel scaffolded polypharmacophores have appended groups, in contrast to traditional therapeutics which have embedded groups, it is possible to control the spatial orientation of the particular appended pharamacophores to obtain the maximum interaction between a pharmacophore and a biological target, and thus exert the maximal effect for a specific condition. In certain embodiments, the scaffold units and/or the pharmacophoric units have one or more modifier units attached thereto, whereby these modifier units are slected to facilitate the delivery, synthesis, activation, absorption, solubility or detection (e.g., by the use of fluorescent or radioactive moieties, or biotin, to name a few) of the scaffolded pharmacophoric units, of the scaffolded pharmacophoric units. In particularly preferred embodiments, the construction of the polypharmacophoric scaffold is amenable to combinatorial chemistry techniques and thus libraries of the inventive scaffolded polypharmacophores can be generated and tested for biological activity. FIG. 3 depicts the contrast between traditional hybrid drugs currently utilized which typically incorporate or integrate two pharmacophoric units within the core structure of the drug, and the inventive scaffolded polypharmacophores, as also depicted by FIG. 2, which are more likely to retain the activity of the individual pharmacophoric groups. As will be appreciated by one of ordinary skill in the art, an agent that is capable of interacting at one or more sites could also be useful as a diagnostic tool or agent.

The inventive scaffolded polypharmacophores as depicted generally in formulas (I) and (IA), libraries thereof, and methods for making these scaffolded polypharmacophores are described in more detail below. Certain other preferred embodiments of these scaffolds and libraries are also depicted in formulas (II), (IIA), (III) and (IIIA) and are described in more detail herein. The discussion of these specific examples, however, is not intended to limit the scope of the present invention.

Scaffolded Polypharmacophores of the Present Invention:

As described earlier, many diseases and conditions are believed to implicate more than one biological site and thus the inventive scaffolded polypharmacophores can be tailored for a specific therapeutic effect. Specific diseases and conditions encompassed by the present invention include, but are not limited to, Parkinson's Disease, Alzheimer's Disease, Huntington's Disease, depression, Attention Deficit Disorder (ADD), autism, obesity, inflammation, rheumatoid diseases, cardiovascular diseases, hypertension, cancer and diabetes, to name a few. In particularly preferred embodiments, the scaffolded polypharmacophores are utilized for conditions in which the dopaminergic neuron is implicated. Other receptors capable of being targeted by the novel polypharmacophores include, but are not limited to serotonin receptors, metabolic glutamate receptors for epilepsy, NMDA receptors, AMPA receptors, Kainate receptors, peptide receptors, and nAGR, mACAR, and AchE receptors.

The present invention provides novel scaffolded polypharmacophores as depicted generally by formulas (I) and (IA):

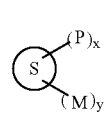
(I)

As depicted in formula (I), S comprises a scaffold unit; P comprises a pharmacophore, wherein x is greater than or equal to 2; M comprises a modifier unit, wherein y is greater than or equal to 0, whereby each one of P and M, for each occurrence, is appended to said scaffold unit and said scaffold unit does not participate directly in the desired pharmacological activity. In addition to modifier units being directly appended to the scaffold, in certain other embodiments additional modifier units (D), wherein a and b, for each occurrence of x or y, are each independently greater than or equal to zero, may also be directly attached to one or more pharmacophores (P) and/or to one or more existing modifier units (M) that are attached to the scaffold to generate the general structure as shown in formula (IA).

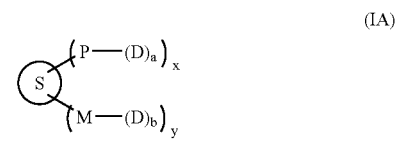
(IA)

It will be appreciated that, in one embodiment, each additional modifier unit can be linked sequentially to either an existing modifier, M, or to a pharmacophore, P, to generate either of the appendages: $S-M-D_1-D_2-D_3$ (etc.) or $S-P-D_1-D_2-D_3$ (etc.). In other embodiments, each additional modifier can be linked directly to the pharmnacophore (P) or modifier unit (M) to generate either of the appendages:

In still other embodiments, each additional modifier can, in certain instances, be linked directly to the pharmacophore or modifier unit, and in other instances also be linked sequentially to generate combinations of appendages as shown for certain exemplary appendages below:

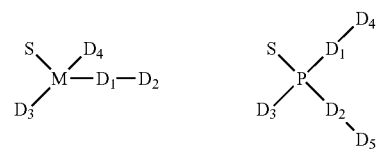

It will be appreciated that a variety of pharmacophoric and modifier units can be appended to the scaffold structures to achieve a desired pharmacological effect. In general, the pharmacophoric unit will be selected to have a desired biological effect associated with a specific condition, and the modifier unit will be selected to facilitate the delivery, detection, synthesis, activation or solubility of an inventive scaffolded polypharmacophore. In preferred embodiments, pharmacophoric units are each independently selected from the group consisting of D-1 agonist, D-2 agonist, D-3 agonist, D-4 agonist, irreversible MAO-inhibitors, reversible MAO-inhibitors, monoamine transporter inhibitors, COMT-inhibitors, MAO-inhibitors, and DA transporter inhibitors.

In a preferred embodiment of the present invention, polypharmacophoric scaffolds and libraries thereof are provided as shown in Formulas (II) and (IIA).

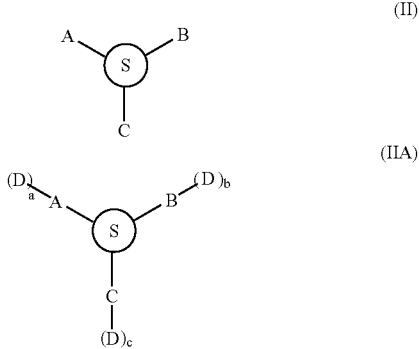

As shown in Formula (II), at least two of A, B, or C comprise a pharmacophore. In certain preferred embodiments, A, B, and C each comprise a pharmacophore. In other preferred embodiments, at least two of A, B, or C comprise a pharmacophore and one of A, B, or C comprises a modifier unit. As shown in Formula (IIA), in certain other preferred embodiments, one or more additional modifier units (D), wherein a, b, and c, are each independently greater than or equal to zero, may also be attached to one or more of A, B, or C. As discussed in more detail above for Formula (I), modifiers (D) may be attached sequentially to one or more of A, B, or C; modifiers may each be directly attached to one or more of A, B, or C; or modifiers may be attached both sequentially and directly to one or more of A, B, or C. In certain preferred embodiments, the novel scaffolded polypharmacophores are utilized to treat conditions in which the dopaminergic system is implicated and the pharmacophoric units are selected from the group consisting of D-1 agonist, D-2 agonist, D-3 agonist, D-4 agonist, irreversible MAO-inhibitors, reversible MAO-inhibitors, monoamine transporter inhibitors, COMT-inhibitors, MAO-inhibitors, and DA transporter inhibitors.

In another exemplary embodiment of the present invention, polypharmacophoric scaffolds and libraries thereof are provided as shown in formulas (III) and (IIIA):

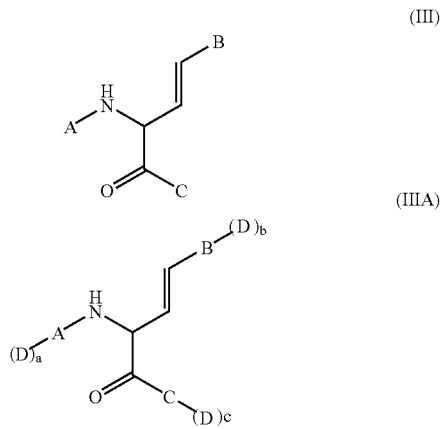

wherein A, B, and C each comprise a desired pharmacophore or modifier unit. It is particularly preferred that two of A, B, or C comprises a pharmacophore and one of A, B, or C comprises a modifier unit. As shown in (IIIA), each of A, B, or C may also have one or more additional modifier units, D, attached thereto, wherein a, b, and c are each independently greater than or equal to zero. As discussed in more detail above for Formula (I), modifiers may be attached sequentially to one or more of A, B, or C; modifiers may each be directly attached to one or more of A, B, or C; or modifiers may be attached both sequentially and directly to one or more of A, B, or C. In certain particularly preferred embodiments, the scaffolded polypharmacophores are utilized to treat conditions in which the dopaminergic neuron is implicated and the pharmacophoric units are preferably selected from the group consisting of D-1 agonist, D-2 agonist, D-3 agonist, D-4 agonist, irreversible MAO-inhibitors, reversible MAO-inhibitors, monoamine transporter inhibitors, COMT-inhibitors, MAO-inhibitors, and DA transporter inhibitors.

Preferred pharmacophores and modifiers for use in the compounds and libraries of the present invention will be described in more detail below.

Pharmacophores

It will be appreciated that a variety of pharmacophoric units can be appended to the scaffold structures to achieve a desired pharmacological effect. As discussed previously, the compounds and libraries of the present invention can be utilized for a variety of conditions and/or diseases that implicate more than one desired site for biological activity, preferably for those biological sites capable of acting in concert. In general, the pharmacophoric units will be selected to have a desired biological effect associated with a particular condition and/or disease, which may involve selection of certain functional group moieties and/or selection of a specific spatial or stereochemical orientation, and will also be selected for certain features, such as specific functional groups that allow facile synthesis of the scaffolded polypharmacophores. In certain embodiments, pharmacophoric units are also selected to enable the modification of the pharmacophoric unit with a modifier unit, as will be described in more detail below.

As will be appreciated by one of ordinary skill in the art, there exists, for many conditions and diseases, a large collection of data and literature describing the pharmacological effects of specific drugs and agents. Instead of utilizing simply one agent to treat a disease or condition, the present invention utilizes several pharmacophoric moieties to treat a disease or condition. Thus, the challenge is to rationally design the target molecules (pharmacophores) in a manner that will retain significant biological activity at each of the targeted sites. Thus, the novel scaffolded polypharmacophores of the present invention utilize known pharmacophores and utilize structure-activity relationships available for specific target sites in the development of the most efficacious pharmacophores. In general, a variety of phamacophoric units can be utilized in the present invention. Specific pharmacophoric moieties include, but are not limited to small organic molecules, peptides, peptidomimetics, nucleotides, and carbohydrates and will be selected based upon the individual condition to be treated and the pharmcological profile.

Figure 4:
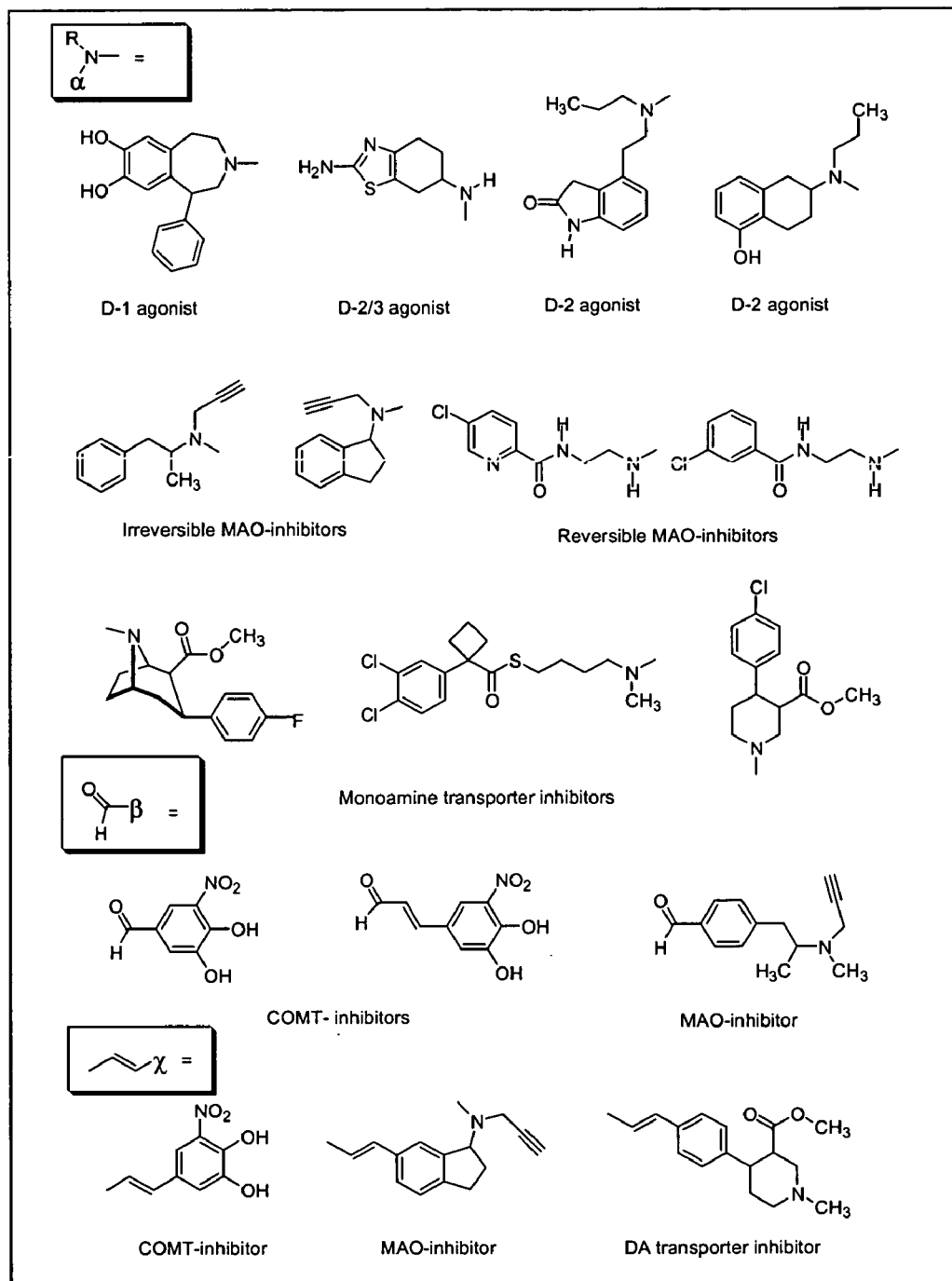
FIG. 4 depicts certain preferred pharmacophoric fragments.

In a preferred embodiment, small organic molecules are utilized in the present invention as pharmacophoric units. The use of small organic molecules may confer increased stability and cell permeability. In a particularly preferred embodiment of the present invention, the subject scaffolded polypharmacophores are utilized to treat Parkinson's Disease. Thus, several classes of pharmacophoric units can be utilized for attachment to the scaffold including, but not limited to dopamine agonists, MAO-inhibitors, monoamine transporter inhibitors, and catechol O-methyl transferase inhibitors. FIG. 4 depicts, for A, B, C in Formula (III), preferred pharmacophoric fragments to be utilized for Parkinson's Disease Therapeutics.

In yet another embodiment, the present invention utilizes amino acids, peptides, peptidomimetics or any combination of peptides or peptidomimetics. A peptide for use in the inventive compounds and methods comprises two or more amino acid residues. In general the abbreviations used herein for designating the amino acids and the protective groups are based on recommendations of the IUPAC-IUB Commission on Biochemical Nomenclature (see Biochemistry (1972) 11:1726–1732). In certain embodiments, the amino acids used in the application of this invention are those naturally occurring amino acids found in proteins, or the naturally occurring anabolic or catabolic products of such amino acids which contain amino and carboxyl groups. The term "amino acid" or "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

It will also be appreciated that unnatural amino acids are within the scope of the present invention, as set forth in, for example, Williams (ed.), Synthesis of Optically Active alpha.-Amino Acids, Pergamon Press (1989); Evans et al., J. Amer. Chem. Soc., 112:4011–4030 (1990); Pu et al., J. Amer. Chem. Soc., 56:1280–1283 (1991); Williams et al., J. Amer. Chem. Soc., 113:9276–9286 (1991); and all references cited therein. Examples of unconventional amino acids include: 4-hydroxyproline, O-phosphoserine, N-acetylserine, N-formylmethionine, 3-methylhistidine, 5-hydroxylysine, and other similar amino acids and imino acids (e.g., 4-hydroxyproline).

Moreover, as will be appreciated by one of ordinary skill in the art, if a desired peptide having a specific activity if found to be unsuitable for various reasons such as chemical instability, or lack of cell permeability, a suitable peptidomimetic can instead be utilized. Such peptidomimetics may comprise close analogs of the original peptide selected as a pharmacophoric unit, or such peptidomimetics may depart from an original pharmacophoric peptide, and this incorporate only a few or none of the original peptide features. Additionally, novel and random "peptide-like" or peptidomimetic compounds may be generated for use as pharmacophoric units to determine those compounds that may have a more desirable activity. Such peptidomimetics can have such attributes as being non-hydrolyzable (e.g., increased stability against proteases or other physiological conditions which degrade the corresponding peptide), increased specificity and/or potency, and increased cell permeability for intracellular localization of the peptidomimetic. For illustrative purposes, peptide analogs of the present invention can be generated using, for example, benzodiazepines (e.g., see Freidinger et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM publisher: Leiden, Netherlands, 1988, p123), C-7 mimics (Huffman et al. in *Peptides: Chemistry and Biology*, G. R. Marshall ed., ESCOM Publisher: Leiden, Netherlands, 1988, p. 105), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill, 1985), β-turn dipeptide cores (Nagai et al. (1985) *Tetrahedron Lett* 26:647; and Sato et al. (1986) *J Chem Soc Perkin Trans* 1:1231), α-aminoalcohols (Gordon et al. (1985) *Biochem Biophys Res Commun* 126:419; and Dann et al. (1986) *Biochem Biophys Res Commun* 134:71), diaminoketones (Natarajan et al. (1984) *Biochem Biophys Res Commun* 124:141), and methyleneamino-modifed (Roark et al. in *Peptides: Chemistry and Biology*, G. R. Marshall ed., ESCOM Publisher: Leiden, Netherlands, 1988, p 134). Also, see generally, Session III: Analytic and synthetic methods, in in *Peptides: Chemistry and Biology*, G. R. Marshall ed., ESCOM Publisher: Leiden, Netherlands, 1988).

In addition to a variety of sidechain replacements, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

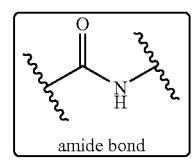

amide bond

Examples of Surrogates

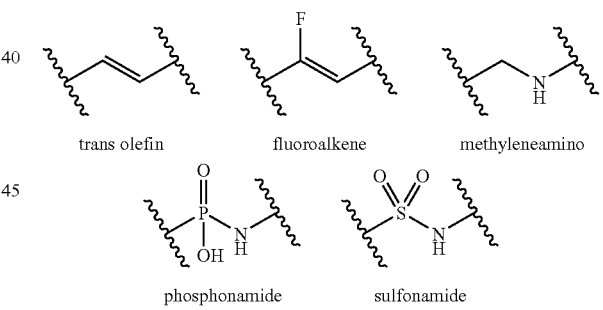

trans olefin      fluoroalkene      methyleneamino phosphonamide      sulfonamide Additionally, peptidomimietics based on more substantial modifications a desired peptide can be used. Peptidomimetics which fall in this category include (i) retro-inverso analogs, and (ii) N-alkyl glycine analogs (so-called peptoids).

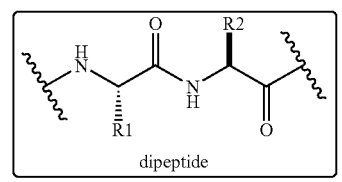

dipeptide

Examples of Analogs

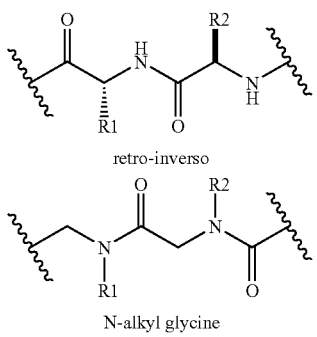

retro-inverso

N-alkyl glycine

Furthermore, the methods of combinatorial chemistry are being brought to bear, e.g., by G. L. Verdine at Harvard University, on the development of new peptidomimetics. For example, one embodiment of a so-called "peptide morphing" strategy focuses on the random generation of a library of peptide analogs that comprise a wide range of peptide bond substitutes.

Many other peptidomimetic structures are known in the art and can be readily adapted for use in the present invention. To illustrate, a "peptidomimetic pharmacophore" may incorporate the 1-azabicyclo[4.3.0]nonane surrogate (see Kim et al. (1997) *J. Org. Chem.* 62:2847), or an N-acyl piperazic acid (see Xi et al. (1998) *J. Am. Chem. Soc.* 120:80), or a 2-substituted piperazine moiety as a constrained amino acid analogue (see Williams et al. (1996) *J. Med. Chem.* 39:1345–1348). In still other embodiments, certain amino acid residues can be replaced with aryl and bi-aryl moieties, e.g., monocyclic or bicyclic aromatic or heteroaromatic nucleus, or a biaromatic, aromatic-heteroaromatic, or biheteroaromatic nucleus.

Modifier Units and Additional Modifier Units

Additionally, as described above, certain embodiments of the present invention include one or more modifier units that may be either attached directly to the scaffold unit or may be attached to existing modifier units and/or pharmacophoric units. For example, modifier units may comprise spacers, scaffold assemblers, delivery modulators, bioactivating groups (that is, they can provide cleavage sites by esterases, enzyme substrate cleavage sites, or pH labile cleavage sites to name a few) and targeting agents, including but not limited to biotin/avidin, biotin, folates, and peptide receptors. Furthermore, modifier units may comprise solid support units in which a linking unit comprising a linker and optionally a spacer can be used to attach the inventive scaffolded polypharmacophore to a solid support.

In one particularly preferred embodiment, a modifier unit, which can be attached directly to the scaffold, or can be attached to pharmacophores or other modifier units, is a targeting moiety. A targeting moiety, as used herein, refers to any molecular structure which assists the inventive scaffolded polypharmacophore in localizing to a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients and proteins can serve as targeting moieties.

The targeting moiety, which assists the construct in localizing to a particular target area, entering a target cell(s), and/or binding to a target receptor, may be selected on the basis of the particular condition or site to be treated. The targeting moiety may further comprise any of a number of different chemical entities. In one embodiment, the targeting moiety is a small molecule.

A particularly preferred targeting moiety for use in the present invention is biotin, a naturally occurring vitamin, which has been shown to localize effectively to tumors and sites of infection. Furthermore, as described in U.S. Pat. No. 5,716,594, imaging agents and therapeutics have been successfully delivered to such sites when coupled to biotin. Another preferred small molecule targeting moiety is folate (see U.S. Pat. No. 5,820,847). Folates are particularly useful in targeting cancer cells, since a variety of carcinomas overexpress folate receptors. See Ladino et al. (Int. J. Cancer 1997, 73(6): 859–6). Riboflavin and its derivatives are other small molecule targeting moieties for targeting delivery of constructs to cancer cells (see, for example, U.S. Pat. No. 5,688,488). Additional nutrients believed to trigger receptor-mediated endocytosis and therefore useful as targeting moieties include carnitine, inositol, lipoic acid, niacin, pantothenic acid, thiamin, pyridoxal, ascorbic acid, and the lipid soluble vitamins A, D, E, and K. A second exemplary type of small molecule targeting moiety includes steroidal lipids, such as cholesterol, and steroidal hormones, such as estradiol, testosterone, etc.

In another embodiment, the targeting moiety may comprise a protein. Particular types of proteins may be selected based on known characteristics of the target site or target cells. For example, the probe can be an antibody either monoclonal or polyclonal, where a corresponding antigen is displayed at the target site. As a second example, certain cells, such as malignant cells and blood cells display particular carbohydroates, for which a corresponding lectin may serve as a targeting moiety. In situations wherein a certain receptor is expressed by the target cells, the targeting moiety may comprise a protein or peptidomimetic ligand capable of binding to that receptor. Proteins corresponding to known cell surface receptors (including low density lipoproteins, transferrin and insulin), fibrinolytic enzymes, anti-HER2, platelet binding proteins such as annexins, and biological response modifiers (including interleukin, interferon, erythropoietin and colony-stimulating factor) are examples of preferred targeting moieties. Also, anti-EGF receptor antibodies, which internalize following binding to the receptor and traffic to the nucleus to an extent, are preferred targeting moieties for use in the present invention to facilitate delivery of Auger emitters and nucleus binding drugs to target cell nuclei.

A number of monoclonal antibodies that bind to a specific type of cell have been developed, including monoclonal antibodies specific for tumor-associated antigens in humans. Among the many such monoclonal antibodies that may be used are anti-TAC, or other interleukin-2 receptor antibodies; 9.2.27 and NR-ML-05 to the 250 kilodalton human melanoma-associated proteoglycan; and NR-LU-10 to a pancarcinoma glycoprotein. An antibody employed in the present invention may be an intact (whole) molecule, a fragment thereof, or a functional equivalent thereof. Examples of antibody fragments are $F(ab')_2$, Fab', Fab, $sF_v$, $F_v$ fragments, and minibodies, which may be produced by conventional methods or by genetic or protein engineering.

Other preferred targeting moieties include sugars (e.g., glucose, fucose, galactose, mannose) that are recognized by target-specific receptors. For example, instant claimed constructs can be glycosylated with mannose residues (e.g., attached as C-glycosides to a free nitrogen) to yield targeted constructs having higher affinity binding to tumors expressing mannose receptors (e.g., glioblastomas and gangliocytomas), and bacteria, which are also known to express mannose receptors (Bertozzi, C R and M D Bednarski Carbohydrate Research 223:243 (1992); J. Am. Chem. Soc. 114:2242,5543 (1992)), as well as potentially other infectious agents.

Additional ligands which may be suitable for use as targeting moieties in the present invention include haptens, epitopes, and dsDNA fragments and analogs and derivatives thereof. Such moieties bind specifically to antibodies, fragments or analogs thereof, including mimetics (for haptens and epitopes), and zinc finger proteins (for dsDNA fragments).

In yet another preferred embodiment, the modifier unit may comprise a spacer moiety or a solid support unit to enable the synthesis of the inventive scaffolded polypharmacophores using the techniques of combinatorial chemistry which will be discussed in more detail below.

Synthesis of Scaffolded Polypharmacophores

As discussed above, the development of the synthesis of the novel scaffolded polypharmacophores preferably take into consideration the ease of synthesis and the ability to incorporate a variety of pharmacophoric units. Thue, in general, the development of a novel scaffolded polypharmacophore for use in a specific treatment first involves selecting specific desired pharmacophoric components, where each of said pharmacophoric components comprises a functionality capable of reacting with a functionality present on the other pharmacophoric components; and reacting said components under conditions to simultaneoulsly generate a scaffolded structure having said pharmacophoric groups appended thereto.

In particularly preferred embodiments, inventive polypharmacophoric scaffolds are prepared by utilizing domino reactions in which a desired number of specific simple components or substrates is provided and upon reaction are capable, through sequences in which a bond formation (or bond-breaking process) is combined with the formation of a new functionality, which again forms a new bond and a new functionality and so on. Domino reactions have been reviewed in the art and a wide variety of reactions can be employed to generate complex molecules in this fashion (Tietze et al. Curr. Opin. Chem. Biol. 1998, 2, 363). Although the use of domino reactions are preferred for the generation of the novel scaffolded polypharmacophores, one of ordinary skill in the art will realize that other reaction schemes may be utilized, although it is preferable that these schemes are able to produce the desired compounds easily and in good yield and are amenable to combinatorial techniques.

It will be appreciated that it is particularly preferred that each of the desired components may be modified so that they may be attached to the solid support. The use of a solid support bound component is particularly preferred because it enables the use of more rapid split and pool techniques to generate larger libraries (e.g., greater than 10,000 members) more easily.

A solid support, for the purposes of this invention, is defined as an insoluble material to which compounds are attached during a synthesis sequence. The use of a solid support is advantageous for the synthesis of libraries because the isolation of support-bound reaction products can be accomplished simply by washing away reagents from the support-bound material and therefore the reaction can be driven to completion by the use of excess reagents. Additionally, the use of a solid support also enables the use of specific encoding techniques to "track" the identity of the inventive compounds in the library. A solid support can be any material which is an insoluble matrix and can have a rigid or semi-rigid surface. Exemplary solid supports include, but are not limited to, pellets, disks, capillaries, hollow fibers, needles, pins, solid fibers, cellulose beads, pore-glass beads, silica gels, polystyrene beads optionally cross-linked with divinylbenzene, grafted co-poly beads, poly-acrylamide beads, latex beads, dimethylacrylamide beads optionally crosslinked with N-N'-bis-acryloylethylenediamine, and glass particles coated with a hydrophobic polymer. One of ordinary skill in the art will realize that the choice of particular solid support will be limited by the compatability of the support with the reaction chemistry being utilized. In one particularly preferred embodiment, a Tentagel amino resin, a composite of 1) a polystyrene bead crosslinked with divinylbenzene and 2) PEG (polyethylene glycol), is employed for use in the present invention. Tentagel is a particularly useful solid support because it provides a versatile support for use in on-bead or off-bead assays, and it also undergoes excellent swelling in solvents ranging from toluene to water.

The compounds of the present invention may be attached directly to the solid support or may be attached to the solid support through a linking reagent. Direct attachment to the solid support may be useful if it is desired not to detach the library member from the solid support. For example, for direct on-bead analysis of biological/pharmacological activity or analysis of the compound structure, a stronger interaction between the library member and the solid support may be desirable. Alternatively, the use of a linking reagent may be useful if more facile cleavage of the inventive library members from the solid support is desired.

Furthermore, any linking reagent used in the present invention may comprise a single linking molecule, or alternatively may comprise a linking molecule and one or more spacer molecules. A spacer molecule is particularly useful when the particular reaction conditions require that the linking molecule be separated from the library member, or if additional distance between the solid support/linking unit and the library member is desired. In one particularly preferred embodiment, photocleavable linkers are employed to attach the solid phase resin to the component. Photocleavable linkers are particularly advantageous for the presently claimed invention because of the ability to use these linkers in in vivo screening strategies. Once the inventive compound is released from the solid support via photocleavage, the inventive polypharmacophore is able to enter the cell. Exemplary photocleavable linkers include, but are not limited to ortho-Nitrobenzyl photolinkers and dithiane protected benzoin photolinkers. One of ordinary skill in the art will realize that the method of the present invention is not limited to the use of photocleavable linkers; rather other linkers may be employed, preferably those that are capable of delivering the desired compounds in vivo.

Combinatorial Methods for the Synthesis of Polypharmacophoric Libraries

According to the method of the present invention, the synthesis of libraries from the above-described scaffold structures can be performed using established combinatorial methods for solution phase, solid phase, or a combination of solution phase and solid phase synthesis techniques. The synthesis of combinatorial libraries is well known in the art and has been reviewed (see, e.g., "Combinatorial Chemistry", Chemical and Engineering News, Feb. 24, 1997, p. 43; Thompson, L. A., Ellman, J. A., Chem. Rev. 1996, 96, 555.)

One of ordinary skill in the art will realize that the choice of method will depend upon the specific number of compounds to be synthesized, the specific reaction chemistry, and the availability of specific instrumentation, such as robotic instrumentation for the preparation and analysis of the inventive libraries. In particularly preferred embodiments, the reactions to be performed on the inventive scaffolds to generate the libraries are selected for their ability to proceed in high yield, and in a stereoselective fashion, if applicable.

In one embodiment of the present invention, the inventive libraries are generated using a solution phase technique. Traditional advantages of solution phase techniques for the synthesis of combinatorial libraries include the availability of a much wider range of organic reactions, and the relative ease with which products can be characterized. In a preferred embodiment, for the generation of a solution phase combinatorial library, a parallel synthesis technique is utilized, in which all of the products are assembled separately in their own reaction vessels. In a particularly preferred parallel synthesis procedure, a microtitre plate containing n rows and m columns of tiny wells which are capable of holding a few milliliters of the solvent in which the reaction will occur, is utilized. It is possible to then use n variants of reactant A, such as a carboxylic acid, and m variants of reactant B, such as an amide to obtain n×m variants, in n×m wells. One of ordinary skill in the art will realize that this particular procedure is most useful when smaller libraries are desired, and the specific wells can provide a ready means to identify the library members in a particular well.

In another more particularly preferred embodiment of the present invention, a solid phase synthesis technique is utilized, in which the desired scaffold structures are attached to the solid phase directly or though a linking unit, as discussed above. Advantages of solid phase techniques include the ability to more easily conduct multi-step reactions and the ability to drive reactions to completion because excess reagents can be utilized and the unreacted reagent washed away. Perhaps one of the most significant advantages of solid phase synthesis is the ability to use a technique called "split and pool", in addition to the parallel synthesis technique, develped by Furka. (Furka et al.,*Abstr. 14th Int. Congr. Biochem.*, Prague, Czechoslovakia, 1988, 5, 47; Furka et al., *Int. J. Pept. Protein Res.* 1991, 37, 487; Sebestyen et al., *Bioorg. Med. Chem. Lett.*, 1993, 3, 413.) In this technique, a mixture of related compounds can be made in the same reaction vessel, thus substantially reducing the number of containers required for the synthesis of very large libraries, such as those containing as many as or more than one million library members. As an example, the solid support scaffolds can be divided into n vessels, where n represents the number species of reagent A to be reacted with the scaffold structures. After reaction, the contents from n vessels are combined and then split into m vessels, where m represents the number of species of reagent B to be reacted with the scaffold structures. This procedure is repeated until the desired number of reagents is reacted with the scaffold structures to yield the inventive library.

The use of solid phase techniques in the present invention may also include the use of a specific encoding technique. Specific encoding techniques have been reviewed by Czarnik. (Czarnik, A. W., *Current Opinion in Chemical Biology*, 1997, 1, 60.) As used in the present invention, an encoding technique involves the use of a particular "identifying agent" attached to the solid support, which enables the determination of the structure of a specific library member without reference to its spatial coordinates. One of ordinary skill in the art will also realize that if smaller solid phase libraries are generated in specific reaction wells, such as 96 well plates, or on plastic pins, the reaction history of these library members may also be identified by their spatial coordinates in the particular plate, and thus are spatially encoded. It is most preferred, however for large combinatorial libraries, to use an alternative encoding technique to record the specific reaction history.

Examples of particularly preferred alternative encoding techniques that can be utilized in the present invention include, but are not limited to, spatial encoding techniques, graphical encoding techniques, including the "tea bag" method, chemical encoding methods, and spectrophotometric encoding methods. Spatial encoding refers to recording a reaction's history based on its location. Graphical encoding techniques involve the coding of each synthesis platform to permit the generation of a relational database. Examples of preferred spectrophotometic encoding methods include the use of mass spectroscopy, fluorescence emission, and nuclear magnetic resonance spectroscopy. In a most preferred embodiment, chemical encoding methods are utilized, which uses the structure of the reaction product to code for its identity. Decoding using this method can be performed on the solid phase or off of the solid phase. One of ordinary skill in the art will realize that the particular encoding method to be used in the present invention must be selected based upon the number of library members desired, and the reaction chemistry employed.

Figure 6:
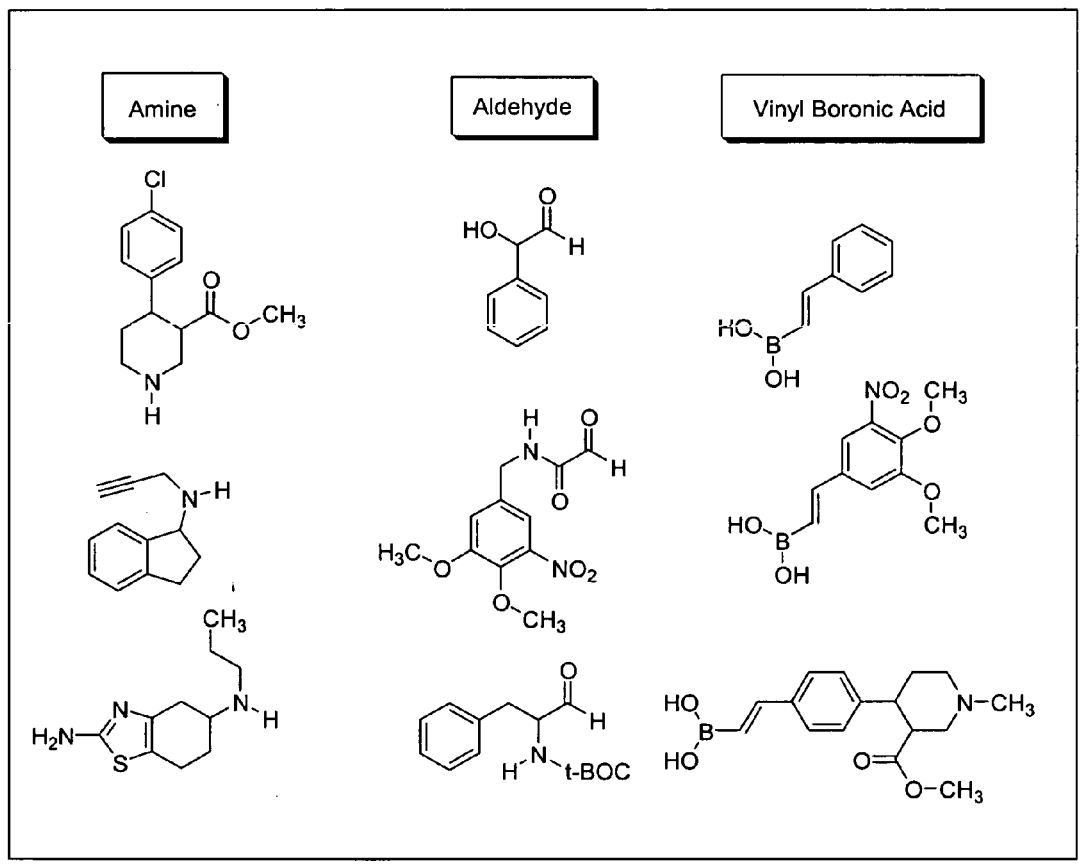
FIG. 6 depicts certain preferred components to be utilized in a combinatorial synthesis.

In an exemplary embodiment of the method of the present invention, a library of at least 25 compounds is prepared, more preferably at least 100 compounds and most preferably at least 500 compounds. Each of the reagents utilized are preferably selected for their ability to generate diversity and for their ability to react in high yield. For example, as depicted in FIG. 6, a combinatorial synthesis may be conducted by selecting specific amine, aldehyde, and vinyl boronic acid components, and reacting these in a combinatorial fashion, using solution phase or solid phase techniques. As one of ordinary skill in the art will realize, the use also of a skip codon, or "blank", at each step yields further diversity. Furthermore, in particularly preferred embodiments, if a solid phase technique is utilized, after each reaction step, the beads are "tagged" to encode the particular reaction choice employed. As will be appreciated by one of ordinary skill in the art, although the use of combinatorial techniques is preferably employed at the stage of scaffold synthesis, combinatorial techniques can also be employed after the scaffolded polypharmacophore has been generated to add modifier units and/or functionalize pharmcophoric units. In but one example, if a peptide pharmacophore is initially generated, this peptide may subsequently be modified and/or lengthened as needed to optimize the pharmacophoric profile.

Subsequent characterization of the library members can be performed using standard analytical techniques, such as mass spectrometry, Nuclear Magnetic Resonance Spectroscopy, and gas chromatograpy. One of ordinary skill in the art will realize that the selection of a particular analytical technique will depend upon whether the inventive library members are in the solution phase or on the solid phase.

Biological Activity of Scaffolded Polypharmacophores

As discussed above, it would be desirable to identify scaffolded polypharmacophores of the present invention that are capable of interacting at a biological site, for example, modulating the biological activity of a biological target, such as a protein, nucleic acid, lipid or combination thereof, whereby such identified compounds are useful in the treatment and/or prevention of diseases or conditions, or are useful as diagnostic agents.

In preferred embodiments, the compounds may be used in in vitro assays, or any other system that allows detection of a chemical or biological function. In general, according to the method of the present invention, one or more inventive scaffolded polypharmcophores is contacted with a biological target having a detectable biochemical activity. Such biological targets include, for example, enzymes, receptors, subunits involved in the formation of multimeric complexes. Such multimeric complex subunits may be characterized by catalytic capabilities (such as, for example, an ability to catalyze substrate conversion), or may alternatively be primarily active in binding to one or more other molecules. The biological target can be provided in the form of a purified or semi-purified composition, a cell lysate, a whole cell or tissue, or even a whole organism. The level of biochemical activity is detected in the presence of the compound and a statistically significant change in the biochemical activity, relative to the level of biochemical activity in the absence of the compound, identifies the compound as a modulator, e.g., inhibitor or potentiator of the biological activity of a target protein. In some cases, particularly where assays are done on whole cells or organisms, the effect of the chemical compound may be to alter the amount, in addition to or instead of the activity, of the particular biological target. "Modulators", therefore, are chemical compounds that alter the level or activity of a particular target. In particularly preferred embodiments, multiple compounds of the inventive scaffolded polypharmacophoric libraries are assayed simultaneously in a high-throughput format, preferably allowing simultaneous analysis of at least 25 compounds, preferably at least 100 compounds, and more preferably at least 500 compounds.

Pharmaceutical Compositions

Once a specific desired effect on a biological target has been associated with a particular compound of the inventive library, one or more of the compounds of the present invention may be utilized as a therapeutic agent for a particular medical condition. A therapeutic agent for use in the present invention may include any pharmacologically active substances that produce a local or systemic effect in animals, preferably mammals, or humans. The term thus means any substance intended for use in the diagnosis, cure, mitigation, treatment or prevention of disease or in the enhancement of desirable physical or mental development and conditions in an animal or human.

As will be appreciated by one of ordinary skill in the art, the therapeutic agent may be administered orally, topically or via injection by itself, or additionally may be provided as a pharmaceutical composition comprising the therapeutic agent and a biologically acceptable carrier. The inventive compositions can be, but are not limited to an aqueous solutions, emulsions, creams, ointments, suspensions, gels, and liposomal suspensions. Particularly preferred biologically acceptable carriers include but are not limited to water, saline, Ringer's solution, dextrose solution and solutions of ethanol, glucose, sucrose, dextran, mannose, mannitol, sorbitol, polyethylene glycol (PEG), phosphate, acetate, gelatin, collagen, Carbopol, and vegetable oils. It is also possible to include suitable preservatives, stabilizers, antioxidants, antimicrobials, and buffering agents, for example including but not limited to BHA, BHT, citric acid, ascorbic acid, and tetracycline. The therapeutic agents of the presently claimed invention may also be incorporated or encapsulated in a suitable polymer matrix or membrane, thus providing a sustained-release delivery device suitable for implantation near the site to be treated locally.

As one of ordinary skill in the art will realize, the amount of the therapeutic agent required to treat any particular disorder will of course vary depending upon the nature and severity of the disorder, the age and condition of the subject, and other factors readily determined by one or ordinary skill in the art.

Other Uses

It will be appreciated that the methods, compounds and libraries of the present invention can be utilized in various disciplines. For example, the scaffolded polypharmacophores of the present invention may also be used as imaging agents or diagnostic agents when labeled with a radionuclide, or fluorescent label. For example, a modifier unit may comprise a radionuclide (such as tritium, iodine-125, iodine-131, iodine-123, iodine-124, astatine-210, carbon-11, carbon-14, nitrogen-13, fluorine-18) may be incorporated into, or attached directly to the core structure, as by halogenation; or the radionuclide (such as Tc-99m, Re-186, Ga-68, Re-188, Y-90, Sm-153, Bi-212, Cu-67, Cu-64, and Cu-62, to name a few) may be attached to a linking group or bound by a chelating group which is then attached to the compound directly, or by means of a linker. Radiolabeling techniques such as these are routinely used in the radiopharmaceutical industry.

Radiolabeled compounds of the invention are generally useful as imaging agents to diagnose neurological disease (e.g., a neurodegenerative disease) or a mental condition or to follow the progression or treatment of such a disease or condition in a mammal (e.g., a human). The radiolabeled compounds of the invention can be conveniently used in conjunction with imaging techniques such as positron emission tomography (PET) or single photon emission computerized tomography (SPECT).

The inventive polypharmacophores may also be useful in the area of materials science. Because of the reactive moieties present in these compounds, molecules such as lipids and other polymeric materials may be attached and thus generate potentially important biomaterials.

Equivalents

Those skilled in the art will recognize, or be able to ascertain using no more than routine experimentation, numerous equivalents to the inventive compositions and methods of use thereof described herein. Such equivalents are considered to be within the scope of this invention and are covered by the following claims. Additionally, examples of particularly preferred embodiments are presented in the examples below and are intended to more particularly describe the present invention, but are not intended to limit the scope of the presently claimed invention.

Exemplification

Synthesis of Scaffolded Polypharmacophores

Figure 5:
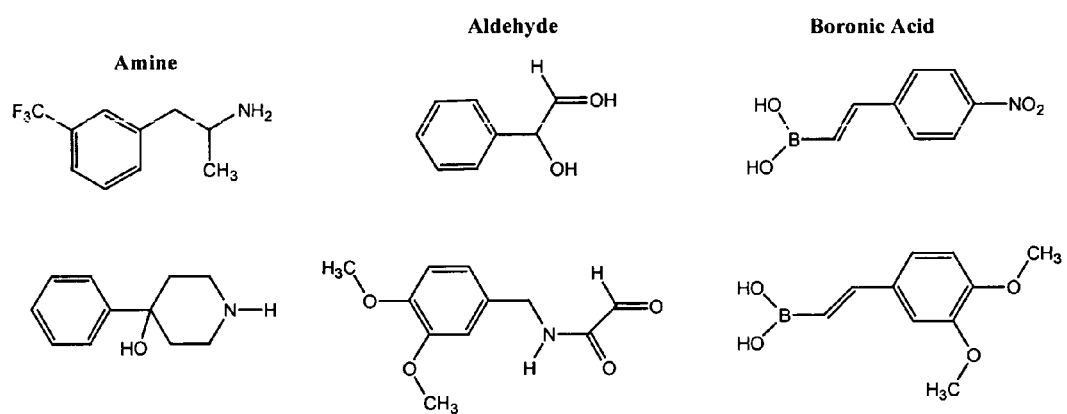
FIG. 5 depicts certain preferred components for the synthesis of scaffolded polypharmacophores.

In but one example of the present invention, novel scaffolded polypharmacophores have been developed for use as agents for Parkinson's Disease. These scaffolded polypharmacophores, in contrast to multi-component "cocktail" drugs, are expected to retain access to the central nervous system and have simplified pharmacokinetic properties. In a preferred embodiment, the scaffold itself can be assembled in a single 3-component reaction (Petasis reaction) from relatively simple materials that provide this approach with pharmacophoric diversity and the ability to be extended to combinatorial expansion. FIG. 5 depicts certain preferred components for the synthesis of these scaffolded polypharmacophores. Scheme 1 below, depicts the simultaneous formation of an exemplary polypharmacophoric scaffold of the present invention. Specific embodiments are described in more detail below, however, one of ordinary skill in the art will appreciate that all equivalents are intended to be encompassed.

Scheme 1

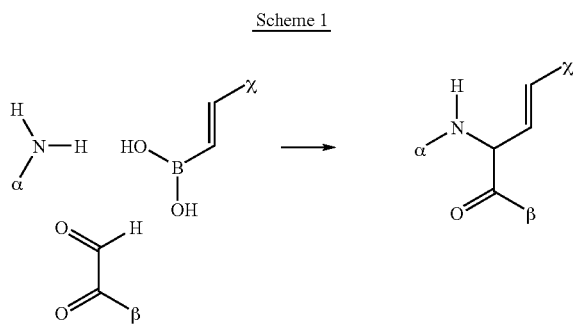

1) Experimental Procedures for the Synthesis of Inventive Compounds a. General Procedure for the Synthesis of α-vinyl-α-amino Acids (Compounds RNH-VII-92, RHN-Z-24, RNH-Z-26, RNH-Z-39, RNH-Z-44, RNH-Z-58, RNH-Z-63, RNH-Z-68, ZHN-84, ZHN-92, ZHN-93, ZNH-94): To a solution of glyoxylic acid hydrate (1.0 equivalents) in 3 mL dichloromethane was added sequentially the amino (1.0 equivalent) and the trans-vinylboronic acid (1.0 equivalent). The reaction was stirred at ambient temperature for 2 hours, filtered and the precipitate was washed with cold dichloromethane. The product was purified by recrystallization from methanol-isopropanol or by column chromatography or silica gel using dichloromethane-methanol as the eluent.

1. Compound RNH-Z24: Isolated yield, 35%; melting point 164–166° C.; NMR (300 MHz) (CD$_3$OD): 7.20–7.54 (m, 10H), 6.95 (d, J=15 Hz, 1H), 6.26 (dd, J=15 Hz, J=10 Hz, 1H), 4.18 (d, J=9.6 Hz, 1H), 3.72 (dd, 2H), 3.1–3.2 (m, 2H), 2.8–2.95 (m, 1H), 2.0–2.1 (m, 3H); C, H, N: calc'd. C=78.5, H=7.17, N=4.36; obsd. C=78.1, H=7.17, N=4.49
2. Compound RNH-Z-26: Yield=85%, melting point=181–182° C.; NMR (300 MHz) (CD$_3$OD) 7.28–7.56 (m, 9H), 6.97 (d, J=16 Hz, 1H), 6.26 (dd, 1H), 4.25 (d, 1H), 3.9 (m, 2H), 3.2–3.65 (m, 4H), 2.38 (m, 2H), 2.0 (m, 2H); Anal. Calcd. C=67.8,H=5.9, N=3.8;Obsd. C=66.0,H=6.1,N=3.9
3. Compound RNH-VII-92: Yield=85%; melting point=187–188 C.; NMR (300 MHz) (CD$_3$OD) 6.9–7.55 (m, 11H), 6.25 (dd, 1H), 4.21 (d, 1H), 3.45 (m, 8H); Anal. Calcd. C=74.5, H=6.8, N=8.7; Obsd. C=74.1, H=6.8, N=8.7 b. General Procedure for the Synthesis of α-vinyl-α-amino Alcohols (Compounds RNH-Z-59, RNH-Z-61, RNH-Z-64, RNH-Z-70): To a solution of glycoaldehyde dimer (0.5 equivalents) in 3 mL ethanol were added the amino (1.0 equivalents) and the vinylboronic acid (1.0 equivalents). The reaction was stirred at ambient temperature for 6–24 hours. The reaction mixture was evaporated to dryness and the resulting solid was purified by column chromatography on silica gel using dichloromethane and methanol as the eluent.

1. Compound RNH-Z-59: Yield=55%; melting point=96–98 C.; NMR (300 MHz) (CD$_3$OD) 7.10–7.50 (m, 10H), 6.62 (d, 1H), 6.29 (dd, 1H), 3.80 (m, 2H), 2.5 (m, 2H), 1.9 (m, 5H)

c. General Procedure for the Synthesis of α-vinyl-α-amino Amides (Compounds RNH-Z-28, RNH-Z-31) (A): To the stirred solution of the α-vinyl-α-amino acid (1.0 equivalents) in 10 mL DMF were added sequentially triethylamine (3 equivalents), 1-hydroxybenzothiazole (1.1 equivalents), the amine (1.1 equivalents) and carbodiimide coupling reagent (1.2 equivalents). The reaction was stirred at ambient temperature for 6–24 hours. The reaction mixture was partitioned between water and ethyl acetate. The organic layer was collected and evaporated to dryness. The resultant residue was purified by chromatography on silica gel using dichloromethane-methanol as the eluent. (B) To the stirred solution of the aminoaldehyde in ethanol (1.0 equivalents) was added sequentially the amine (1.0 equivalent) and the vinylboronic acid (1.0 equivalent). The reaction was allowed to proceed at ambient temperature for 6–24 hours. The reaction mixture was evaporated to dryness and the residue was purified by column chromatography using dichloromethane-methanol as the eluent.

1. Compound RNH-Z-28: Yield=50%; NMR (300 MHz) (CD$_3$OD); 7.1–7.5 (m, 10 H); 6.90 (d, 1H); 6.36 (dd, 1H); 4.04 (d, 1H); 3.0–3.4 (m, 10H), 2.5 (m, 1H), 2.2–2.4 (m, 2H); 1.8 (m, 4H)
2. Compound RNH-Z-31: Yield=60%; NMR (300 MHz) (CD$_3$OD); 7.1–8.1 (m, 11H); 6.67 (d, 1H); 6.26 (dd, 1H); 3.52 (d, 1H), 3.0–3.1 (m, 2H); 2.5 (m, 1H); 2.1–2.2 (m, 2H); 1.7 (m, 4H)

2) Generation of Combinatorial Libraries of Inventive Polypharmacophores

Figure 7:
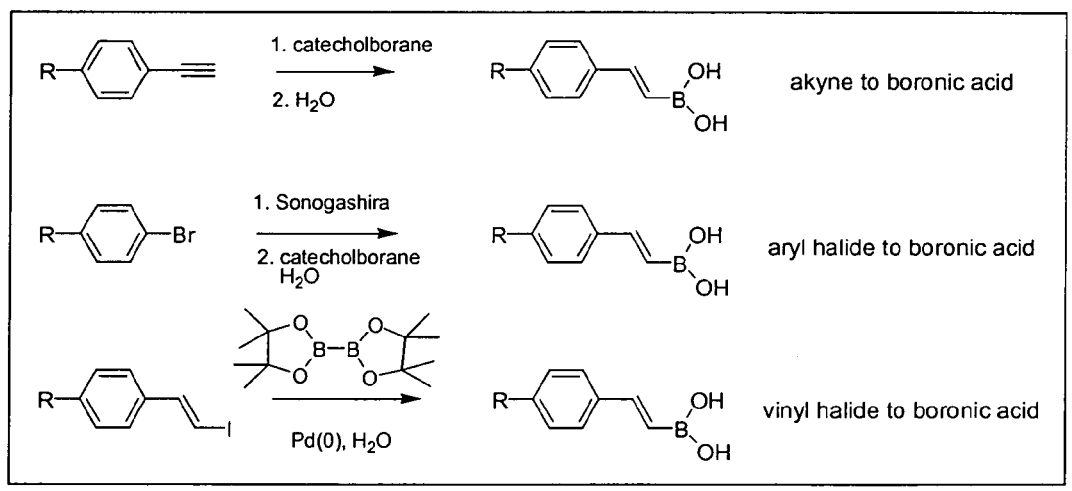
FIG. 7 depicts the representative synthesis of certain preferred vinyl boronic acids.
Figure 8:
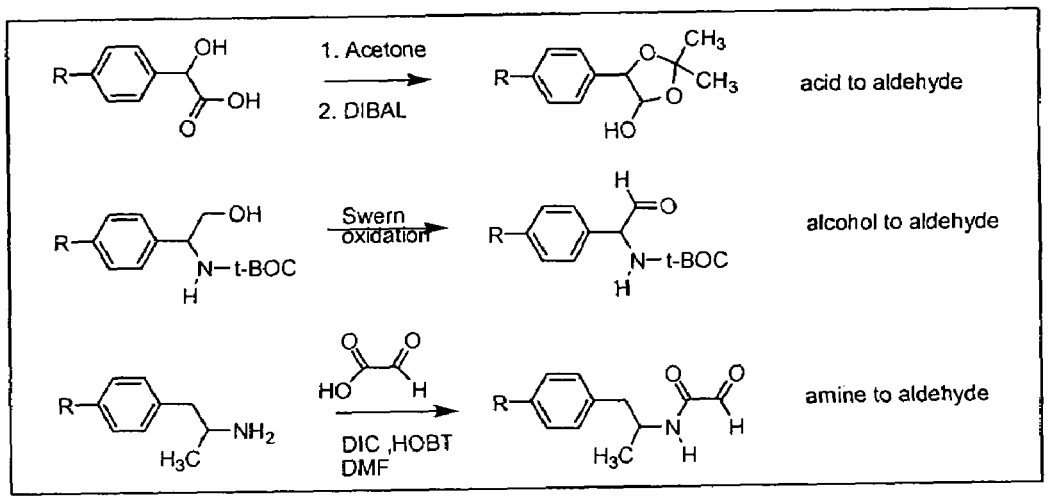
FIG. 8 depicts the representative synthesis of certain preferred aldehydes.
Figure 9:
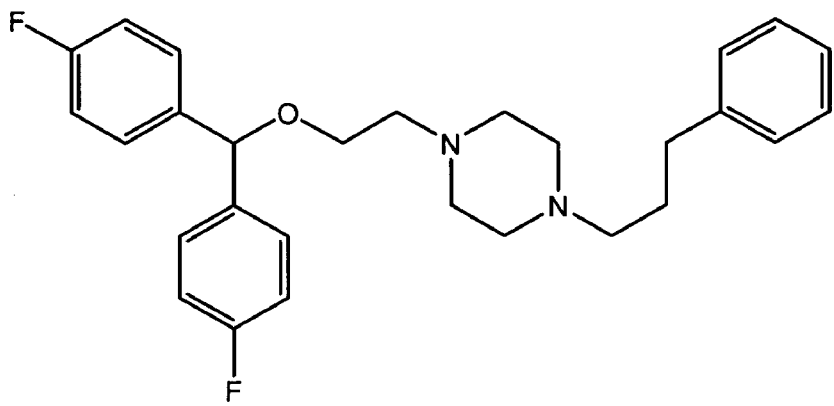
FIG. 9 depicts certain preferred scaffolded polypharmacophores.
Figure 9:
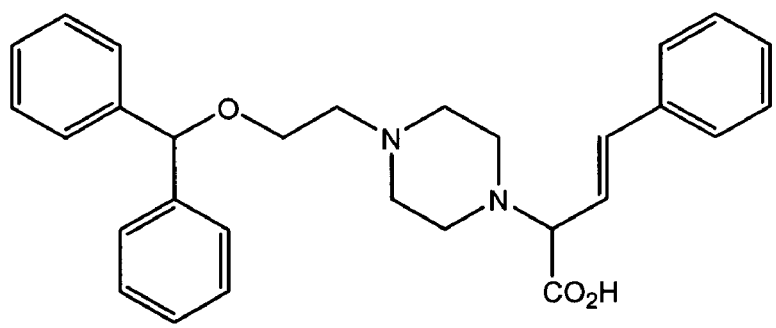
Figure 9:
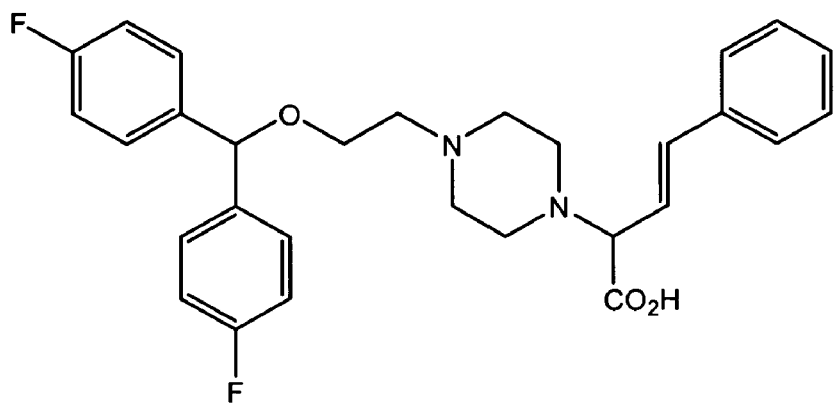
Figure 10:
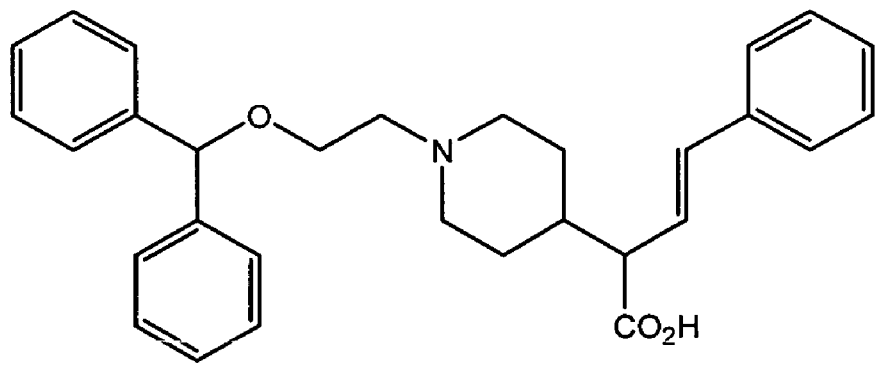
FIG. 10 depicts certain preferred scaffolded polypharmacophores.
Figure 10:
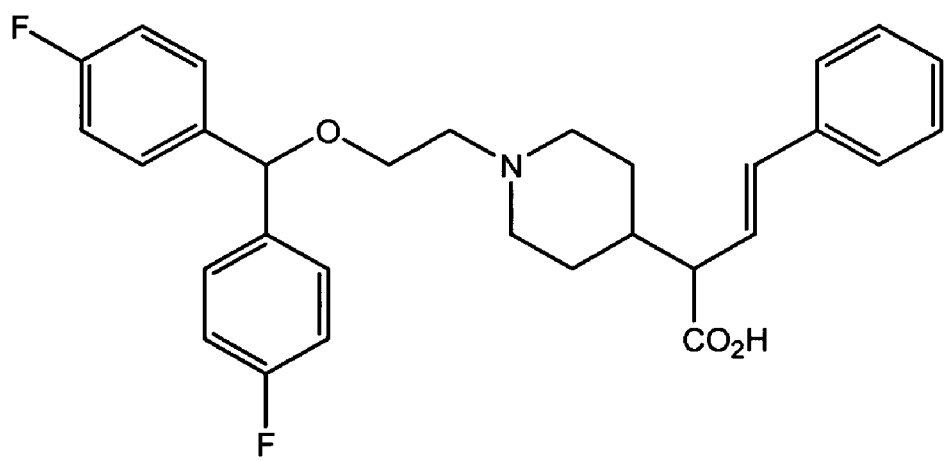
Figure 11:
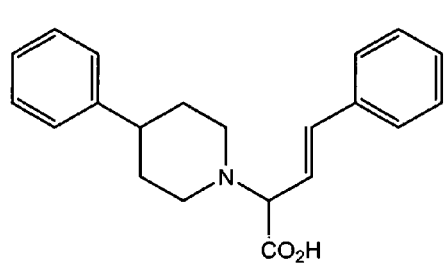
FIG. 11 depicts certain preferred scaffolded polypharmacophores.
Figure 11:
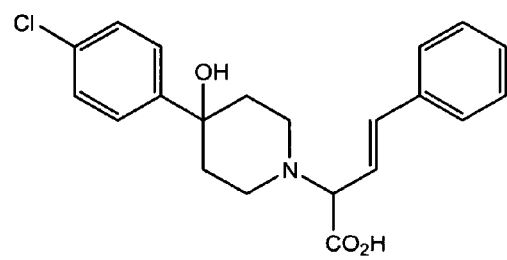
Figure 11:
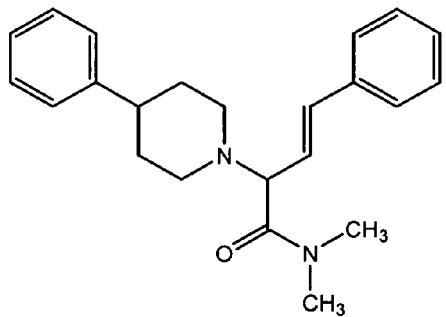
Figure 11:
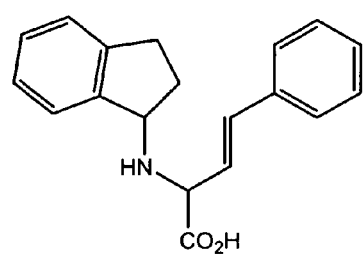
Figure 12:
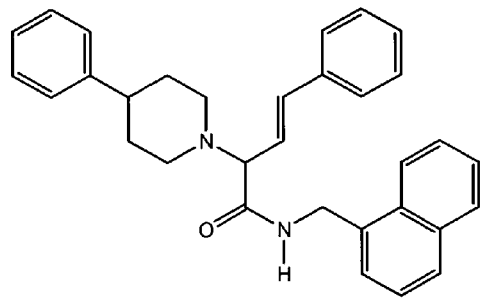
FIG. 12 depicts certain preferred scaffolded polypharmacophores.
Figure 12:
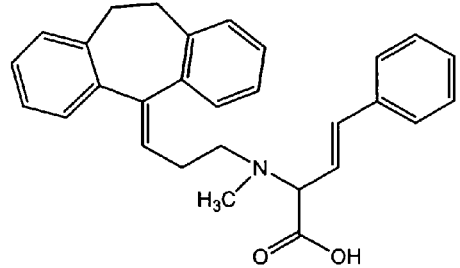
Figure 12:
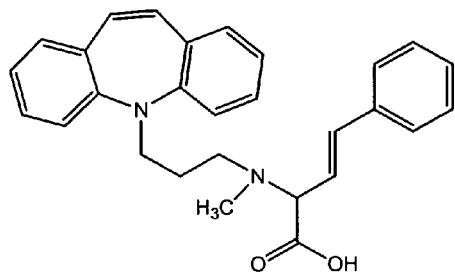
Figure 12:
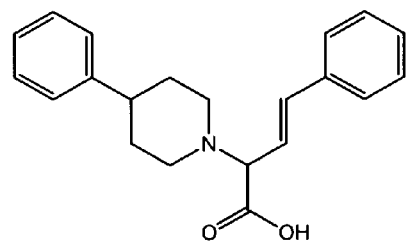
Figure 12:
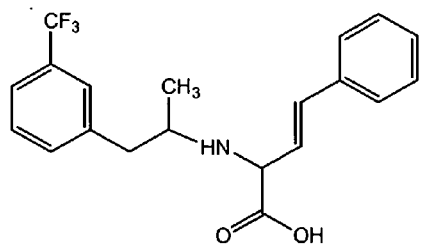
Figure 13:
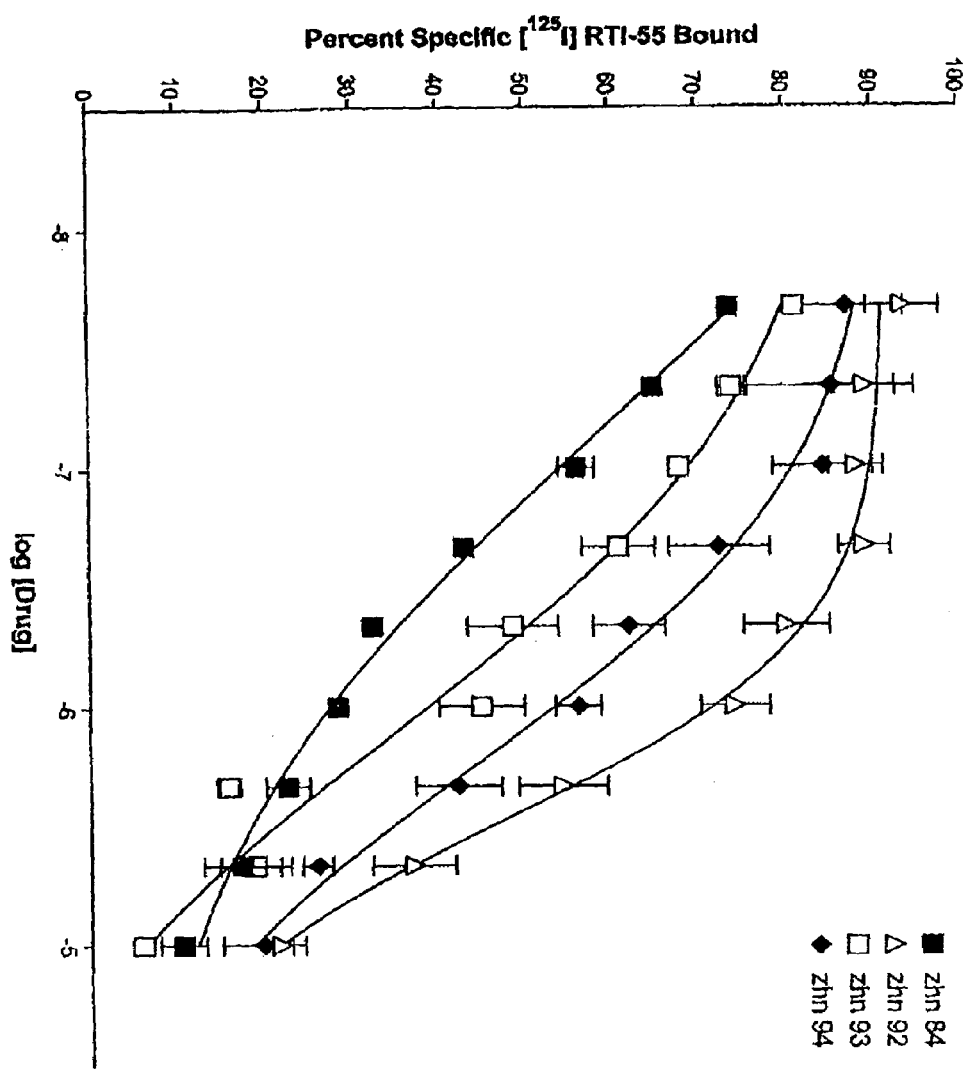
FIG. 13 depicts the percent specific [$^{125}$I]RTI-55 bound vs. log [drug].
Figure 14:
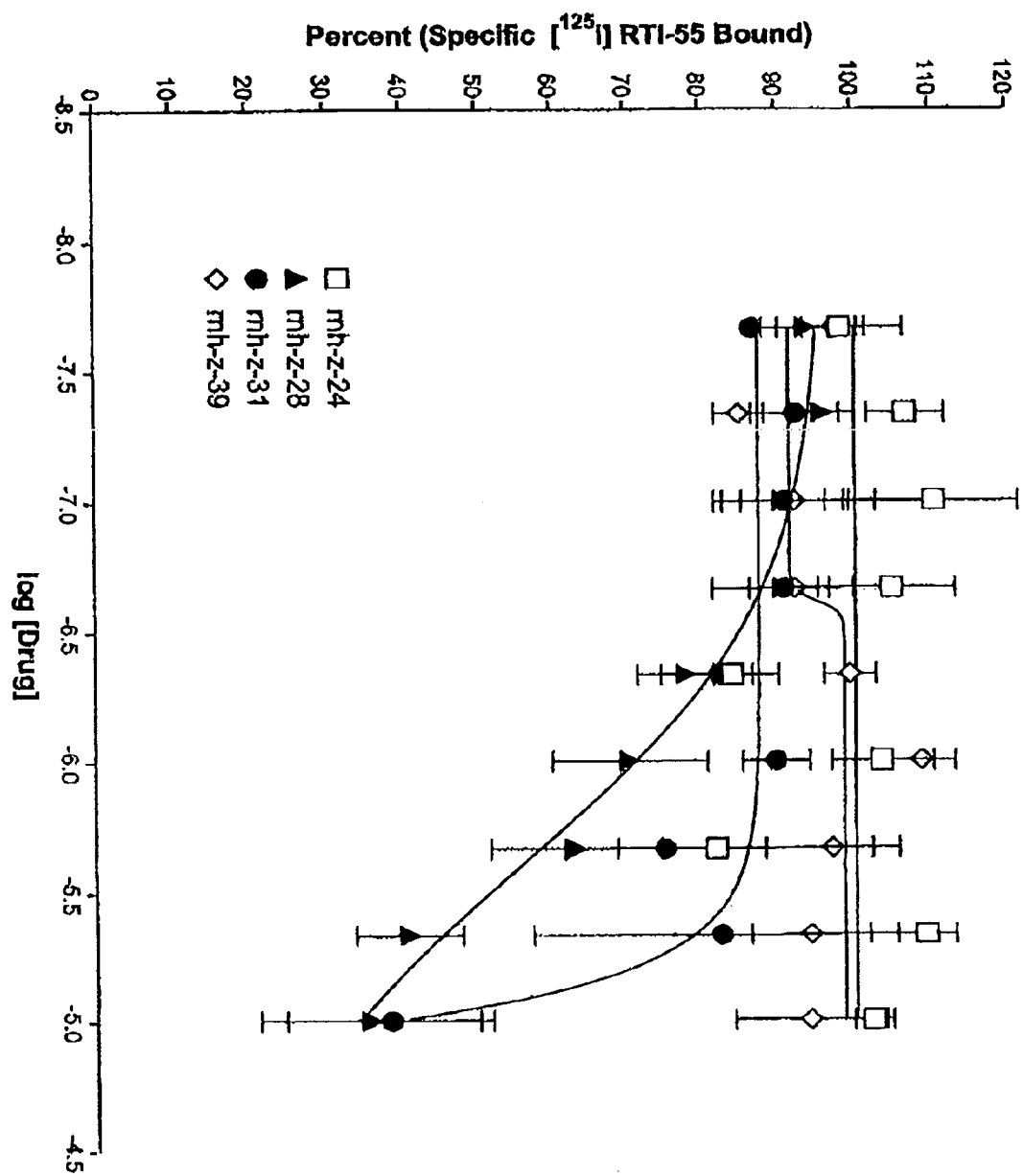
FIG. 14 depicts the percent specific [$^{125}$I]RTI-55 bound vs. log [drug].
Figure 15:
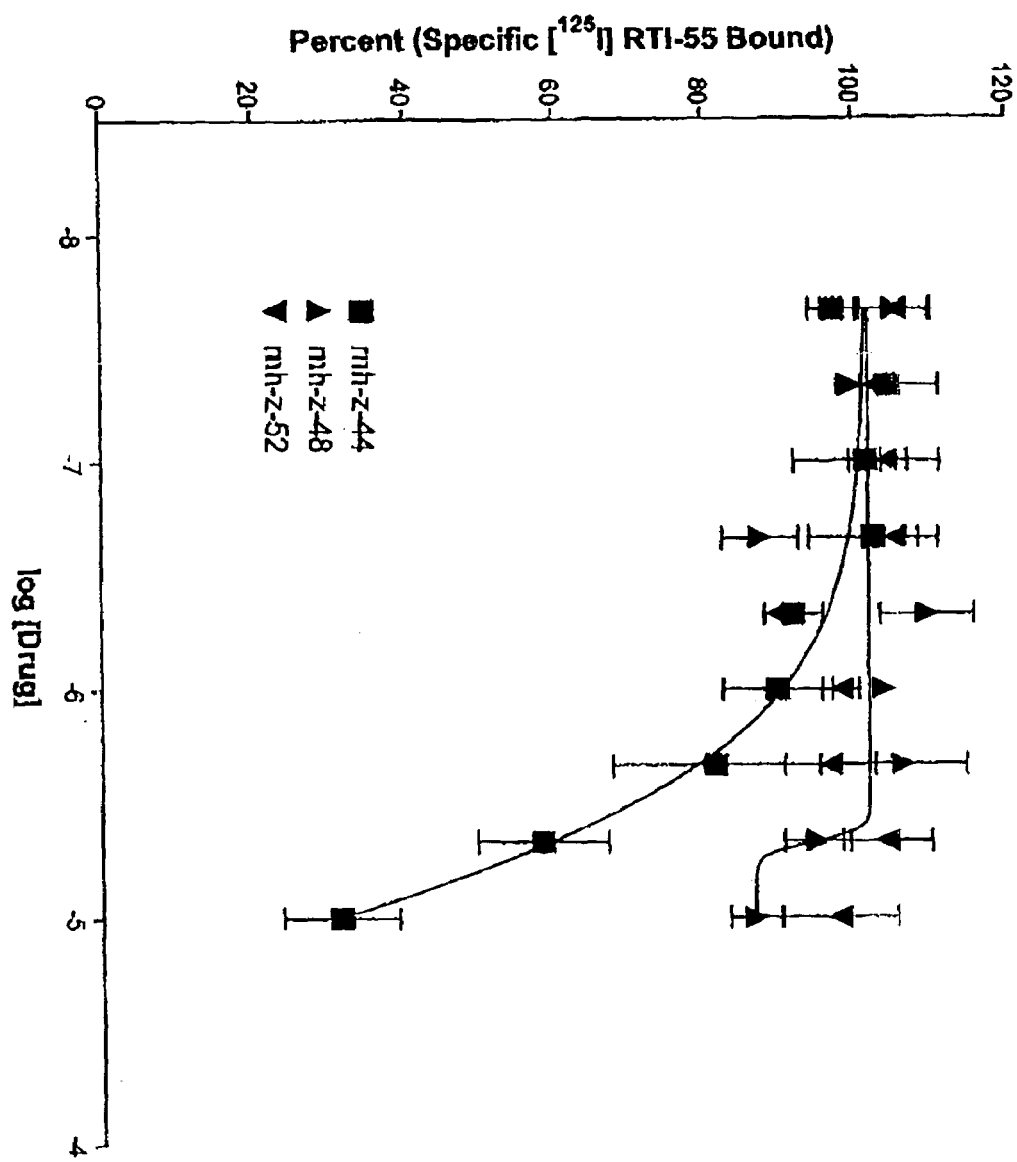
FIG. 15 depicts the percent specific [$^{125}$I]RTI-55 bound vs. log [drug].
Figure 16:
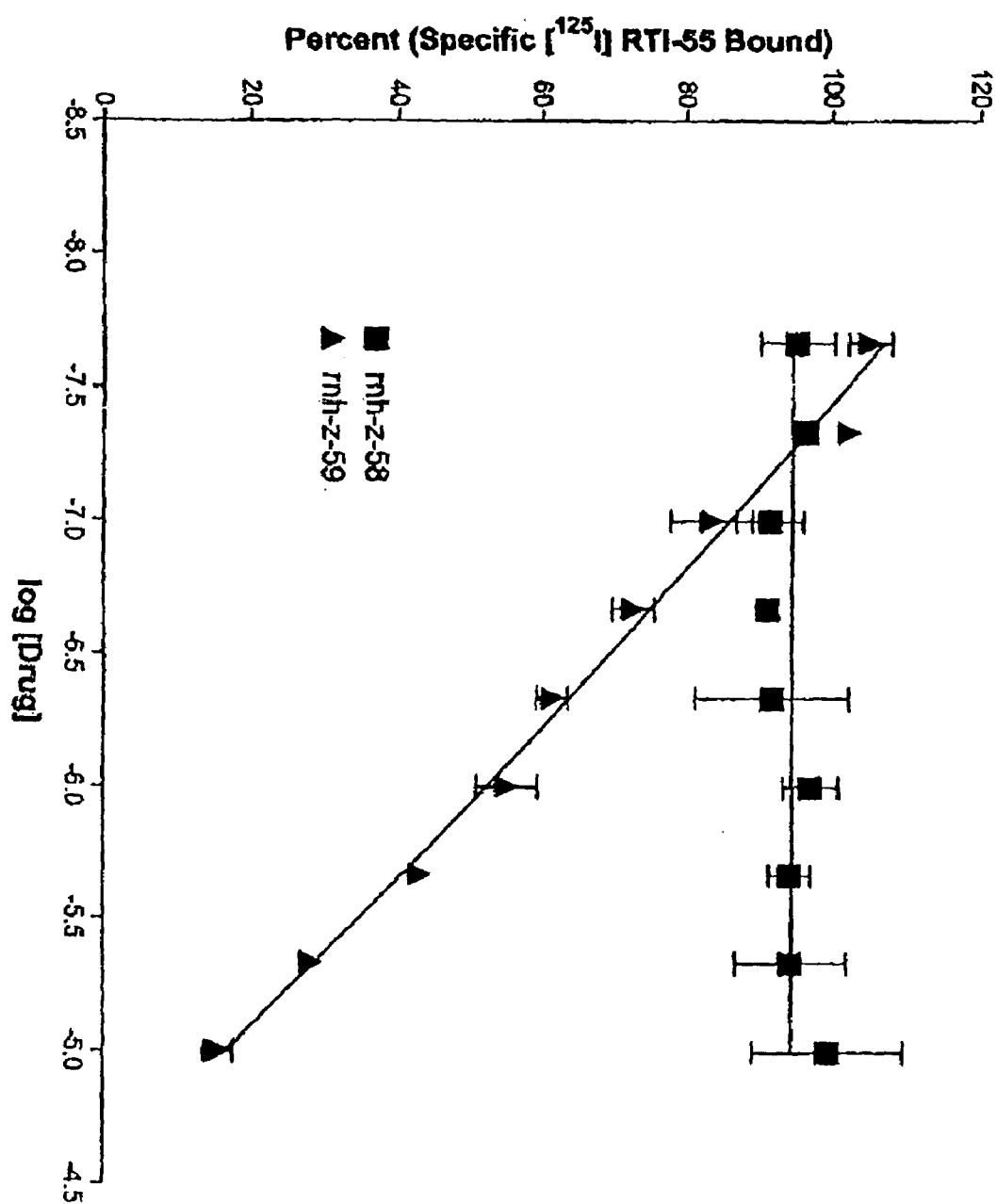
FIG. 16 depicts the percent specific [$^{125}$I]RTI-55 bound vs. log [drug].
Figure 17:
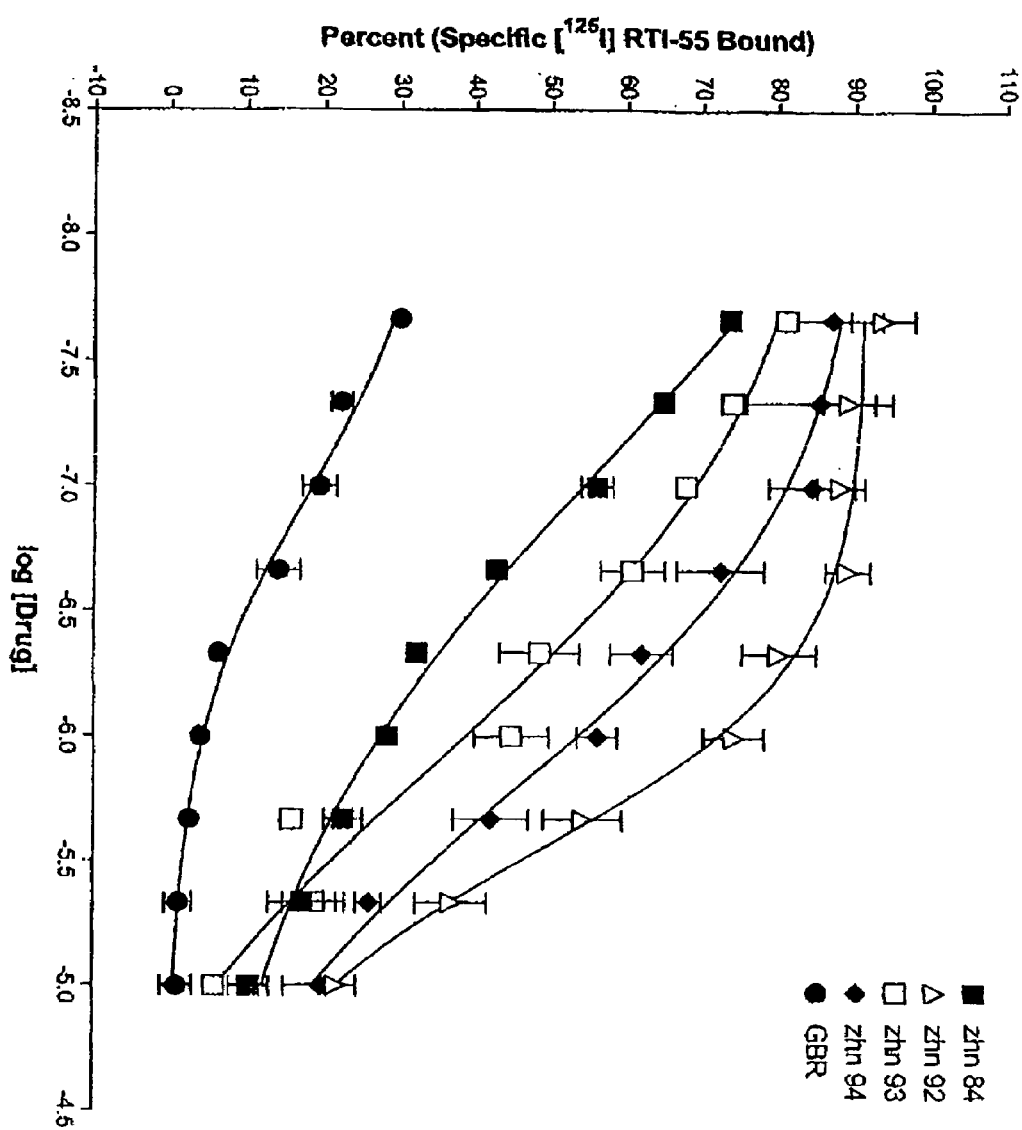
FIG. 17 depicts the percent specific [$^{125}$I]RTI-55 bound vs. log [drug].

In an exemplary embodiment of the present invention, a directed combinatorial library can be prepared for use as agents for treating Parkinson's Disease. The reactions and conditions described in the above examples can also be utilized to generate these combinatorial libraries of polypharmacophores. These libraries can be prepared in the solution phase or on the solid phase. We have selected for the amine component of the scaffold a D$_2$ agonist, an irreversible MAO inhibitor, and a DAT inhibitor. The aldehyde and vinylboronic acid components incorporate inhibitors of COMT, MAO, and DAT. FIG. 6 depicts the use of certain exemplary fragments for a small combinatorial library for use as agents for Parkinson's Disease, although it will be appreciated that other pharmacophores can also be utilized in the present invention. Although a number of secondary amines, aldehydes and vinyl boronic acids shown in FIG. 6 are commercially available, many of the starting materials require synthesis from other intermediates. Representative syntheses of certain components used in the inventive library are described in FIGS. 7, and 8.

The synthesis of the mini-directed library is preferably performed on a scale which will provide approximately 0.1–1.0 mmoles of each target compound. Using the reaction conditions described above, solutions of the 3 representative amines, 3 aldehydes and 3 vinylboronic acids for 3×3×3 library are prepared. The solvent is removed by rotary evaporation and each of the twenty seven compounds are isolated by column chromatography on silica gel and recrystallized as their maleate or fumarate salt. Each compound is also characterized by $^1$H-NMR, FTIR and HRMS (or elemental analysis) to confirm its structural identity. Clearly, these syntheses will generate mixtures of enantiomers and diastereomers, which can be separated using techniques well-known in the art of organic synthesis, if desired.

3) Biological Evaluation of Agents in Therapeutically Relevant Biological Assays To evaluate the potential efficacy of the target compounds and libraries of compounds, in vitro screening assays are utilized against the biological targets of the appended pharmacophores. For example, compounds that contain a dopamine receptor agonist, COMT inhibitor and a MAO inhibitor pharmacophore within their structure are evaluated in those screens. The compounds will be compared to their separate component to determine the extent to which the desired biological activity is retained or enhanced. After this initial screening, the compounds are then screened more extensively to determine their broader pharmacological profile since this may identify additional benefits or potential side effects.

Competitive binding assays are utilized to determine the affinity of the ligands for the dopamine D-1 and $D_2$ receptors (human recombinant receptor with [$^3$H]SCH-23390 and [$^3$H]spiperone as the radioligands). Efficacy of ligands which demonstrate $K_d$ values<$10^{-7}$ are determined in functional assays appropriate to the receptor subtype. Inhibition of DAT binding (human recombinant protein in CHO cells) and [$^3$H]DA reuptake in CHO-K1/hDAT cells that have been stably transfected. The ability of the target ligands to inhibit COMT are determined using the enzyme preparation obtained from rats, specifically looking for the reduction in the metabolism of 3,4-dihydroxybenzoic acid to generate $IC_{50}$ values. Inhibition of MAO -B is determined in preparations obtained from rat liver using [$^3$H]DA as the standard substrate to yield the $IC_{50}$ values. Selected compounds can also be more broadly screened as potential receptor ligands.

As depicted in Table 1, the drug effects on specific [$^{125}$I]RTI-55 Binding to the Human Dopamine Transporter were examined. To characterize drug interactions with the human dopamine transporter (hDAT), drugs (approximately 30 nM to 10 µM) were incubated with a membrane preparation from HEK-293 cells stably expressing the recombinant hDAT, [$^{125}$I]RTI-55 (34 pM), and buffer in a final volume of 250 µl. Independent assays were conducted 2 to 3 times with duplicate determinations. The Cheng-Prusoff equation was used to convert $IC_{50}$ values to $K_i$ values. Data in Table 1 represent averaged values +/− range or +/− the s.e.m. for 2 or 3 experiments, respectively. The value for GBR-12935 is taken from Eshleman et al., 1999.

TABLE 1

Drug Effects on Specific [$^{125}$I]RTI-55 Binding to the Human Dopamine Transporter

| Drug | $K_i$ value (nM) | Hill Coefficient |
|---|---|---|
| ZHN-84 | 75 ± 39 | −0.5 ± 0.2 |
| ZHN-92 | 3713 ± 1247 | −1.2 ± 0.2 |
| ZHN-93 | 727 ± 291 | −1.0 ± 0.3 |
| ZHN-94 | 2784 ± 1250 | −0.8 ± 0.2 |
| RNH-Z-28 | 3922 ± 1245 | −2.1 ± 0.6 |
| RNH-Z-31 | 7727 ± 3074 | −7.0 ± 4.5 |
| RNH-Z-44 | 3300 ± 855 | −2.2 ± 0.9 |
| GBR-12935 | 14 ± 3 | −1.6 ± 0.8 |

Additionally, FIGS. 13–17 depict the percent specific [$^{125}$I] RTI-55 bound versus the log[drug].

Additionally, as shown in Table 2, the ability of specific compounds to bind to multiple receptors is examined.

TABLE II

| Compound | [$^{125}$I]RTI-55 Binding in HEK hDAT Membranes $K_i$ (nM) sem Hill slope | [$^3$H]DA Uptake in HEK hDAT cells $IC_{50}$ (nM) sem | [$^{125}$I]RTI-55 Binding in HEK hSERT Membranes $K_i$ (nM) sem Hill slope | [$^3$H]5HT Uptake in HEK-hSERT cells $IC_{50}$ (nM) sem | [$^{125}$I]RTI-55 Binding in HEK-hNET Membranes $K_I$ (nM) sem Hill slope | [$^3$H]NE Uptake in HEK-hNET cells $IC_{50}$ (nM) sem |
|---|---|---|---|---|---|---|
| GBR-12935 | 73 ± 39<br>−0.44 ± 0.09 | 18 ± 3 | 2091 ± 756<br>−1.47 ± 0.36 | 3710 ± 1429 | 628 ± 59<br>−0.90 ± 0.07 | 165 ± 17 |
| ZHN-84 | 74 ± 39<br>−0.52 ± 0.17 | 89 ± 40 | >10 µM | >10 µM | >10 µM | 805 ± 206 |
| ZHN-92 | 3713 1247<br>−1.15 0.15 | 2013 ± 428 | >10 µM | >10 µM | >10 µM | 113 ± 15 |
| ZHN-93 | 727 ± 291<br>−1.02 ± 0.30 | 182 ± 59 | >10 µM | >10 µM | 4540 ± 1539<br>−1.78 ± 0.65 | 117 ± 20 |
| ZHN-94 | 2784 ± 1250<br>−0.78 ± 0.17 | 385 ± 111 | >10 µM | >10 µM | >10 µM | 2195 ± 470 |
| RNH-Z-24 | >10 µM | >10 µM | >10 µM | >10 µM | >10 µM | 204 ± 85 |
| RNH-Z-28 | 3922 ± 1245<br>−2.09 ± 0.60 | 4045 ± 1630 | >10 µM | >10 µM | >10 µM | 211 ± 65 |
| RNH-Z-31 | 7727 ± 3074<br>−7.00 ± 4.54 | >10 µM | >10 µM | >10 µM | >10 µM | >10 µM |
| RNH-Z-39 | >10 µM | >10µM | >10 µM | >10 µM | 2920 ± 1226<br>−0.96 ± 0.17 | >10 µM |
| RNH-Z-44 | 3300 ± 855<br>−2.16 ± −0.89 | 1820 ± 819 | >10 µM | >10 µM | >10 µM | >10 µM |
| RNH-Z-48 | >10 µM | >10 µM | >10 µM | >10 µM | >10 µM | >10 µM |
| RNH-Z-52 | >10 µM | >10 µM | >10 µM | >10 µM | >10 µM | >10 µM |
| RNH-Z-58 | >10 µM | >10 µM | >10 µM | >10 µM | >10 µM | >10 µM |
| RNH-Z-59 | >10 µM | 857 ± 168 | >10 µM | >10 µM | >10 µM | >10 µM |

As will be appreciated by one of ordinary skill in the art, the results for each of the compounds evaluated can be compiled to build structure activity relationships at each of the targeted sites. The profile contains, in addition to the physicochemical and spectroscopic properties of the compound, the biological activity of the material, e.g., $K_d$, $K_i$, $IC_{50}$ values, compared to a mono-pharmacophoric standard. The structure activity relationships obtained from the initial studies can serve to direct the synthesis of subsequent larger directed libraries of compounds with improved properties and as the basis for the selecting candidate agents for pre-clinical evaluation. Although the examples above are directed to receptor sites believed to be involved in Parkinson's Disease, depression, substance addiction, ADD, ADHD, Huntington's Disease, and schizophrenia, it will be appreciated by one of ordinary skill in the art that other assays can be utilized to examine the biological effects of other polypharmacophoric compounds, that are targeted for different conditions. For example, other conditions include, but are not limited to asthma, inflammation, CHF, and hypertension.

In certain preferred embodiments, properties that one would expect for the hybrid pharmacophoric compounds is activity against two of the target sites equal to that of the isolated pharmacophoric unit and activity against a third target site with a reduction of 0.5 log units in potency as compared to the unsubstituted fragment. In another preferred embodiment, the desired properties for the hybrid pharmacophoric compounds comprise three pharmacological activities that are reduced by 1 log unit. In a particularly preferred embodiment, optimal properties that one would expect for the hybrid pharmacophoric compounds comprises activity against each of the target sites equal to that of the isolated pharmacophoric unit. For example, if the hybrid contains a dopamine agonist, DAT inhibitor and a COMT inhibitor, as components, the intact molecule would preferably express all three activities in approximately the same potencies as seem for each fragment. It will be appreciated that preferred polypharmacophoric compounds, in addition to comprising desirable activity against each of the target sites, also have desirable safety profiles. Evaluation and interpretation of the data enables the determination of which components of the hybrid would require enhancement or reduction. This information will also influence the synthetic strategy for desired combinatorial libraries and compounds.

REFERENCES

1. Colcher, A.; Simuni, T. Clinical Manifestations of Parkinson's Disease. *Med. Clin. No. Am.* 1998, 83, 327–347.
2. Lang, A. E.; Lozano, A. M. Parkinson's Disease. *N. Engl. J Med.* 1998, 339, 1030–1050 and ref. therein.
3. Hubble, J. P. Novel Drugs for Parkinson's Disease. *Med. Clin. No. Am.* 1999, 83, 525–536.
4. Hauser, R. A.; Zesiewicz, T. A. Management of Early Parkinson's Disease. *Med. Clin. No. Am.* 1999, 83, 393–414.
5. Hagan, J. J.; Middlemiss, D. N.; Sharpe, P. C.; Poste, G. H. *Parkinson's Disease: Prospects for Improved Drug Therapy. TIPS* 1997,18, 156–163.
6. Lozano, A. M.; Lang, A. E.; Hutchinson, W. D.; Dostrovsky, J. O. New Developments in Understanding the Eitology of Parkinson's Disease and its Treatment. *Curr. Opin. Neurobiol.* 1998, 8, 783–790 and refs. therein.
7. Hughes, A. J. Drug Treatment of Parkinson's Disease in the 1990's. *Drugs* 1997, 3, 195–205.
8. Stacy, M. Managing Late Complications of Parkinson's Disease. *Med. Clin. No. Am.* 1999, 83, 469–474.
9. Siderowf, A.; Kurlon, R. Monoamine Oxidase and Catechol O-methyl Transferase Inhibitors. *Med. Clin. No. Am.* 1999, 83, 443–463.
10. Mitlan, M.; Peglion, J. -L. (ADIR et al.). Aminated 6, 7, 8, 9-tetrahydrocyclopenta [a] naphthalene- and 2,3-dihydrocyclopenta [e] indene derivatives. Process for their preparation and pharmaceutical compositions containing them. EP 870759, JP 98287631 1998.
11. Chorev, M. et al. (Teva Pharmaceutical Industries). Aminoindan derivatives. WO 98/27055 1998.
12. Graul, A.; Castaner, J. Brasofensine sulfate. *Drugs of the Future* 1999, 24, 128–132.
13. Cheetham, S. C., et al. (Knoll AG). Substituted 4-arylmethylene-2-imino-2,3-dihydrothiazoles and derivatives and their pharmaceutical use. WO 98/41528 1998.
14. Budygin, E. A.; Gainetdinov, R. R.; Kilpatrick, M. R.; Rayevsky, K. S.; Mannisto, P. T.; Wrightman, R. M. Effect of tolcapone, a catechol-O-methyltransferase inhibitor, on striatal dopaminergic transmission during blockade of dopamine uptake. *Eur. J Pharm.* 1997, 370, 125–131.
15. Bonafati, V.; Meco, G. New, selective catechol-O-methyltransferase inhibitors as therapeutic agents in Parkinson's Disease. *Pharmacol. Ther.* 1999, 81, 1–36.
16. Calabrese, V. P.; Lloyd, K. A.; Brancazio, P.; Cefali, E.; Martin, P.; Wall, J. Jr.; Sica, D. N-0923, a novel soluble dopamine D-2 agonist in the treatment of parkinsonsim. Mov. Disorder 1998, 13, 768–774.Tietze, L. F.; Lieb, M. E. Domino Reactions for Library Synthesis of Small Molecules in Combinatorial Chemistry. *Curr. Opin. Chem. Biol.* 1998, 2, 363–371.
17. Tietze, L. F.; Lieb, M. E. Domino Reactions for Library Synthesis of Small Molecules in Combinatorial Chemistry. *Curr. Opin. Chem. Biol.* 1998, 2, 363–371. (a) Petasis, N.; Akritopoulou, I. The boronic acid mannich reaction: a new method for the synthesis of geometrically pure allylamines. Tet. Lett. 1993, 34, 583–586. (b) Petasis, N.; Zavialov, I. A. A New and Practical Synthesis of α-amino acids from alkenyl boronic acids. *J. Am. Chem. Soc.* 1997, 119, 445–446. (c) Petasis, N.; Zavialov, I. A. Highly Stereocontrolled One-Step Synthesis of anti-β-amino alcohols from Organoboronic Acids, Amines and α-hydroxy aldehydes. J. Am. Chem. Soc. 1998, 120, 11798–11799.
18. Thorand, S.; Krause, N. Improved Procedures for the Palladium-catalyzed coupling of terminal alkynes with aryl bromides (Songashira coupling). *J. Org. Chem.* 1998, 63, 8551–8553.
19. Brown, H. C.; Gupta, S. K. Catecholborane (1,3,2-benzodioxaborole) as a new, general monohydroboration reagent for alkynes. A convenient synthesis of alkeneboronic esters and acids from alkynes via hydroboration. *J. Am. Chem. Soc.* 1972, 94, 4370–4371.

Each of the references cited above is incorporated by reference.

We claim:

1. A polypharmacophore selected from the group consisting of:

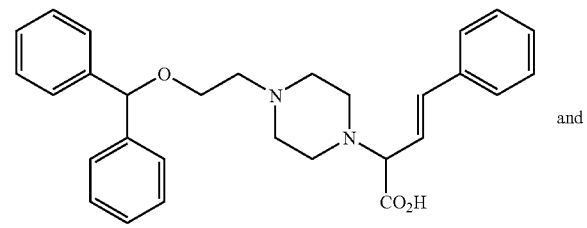

and

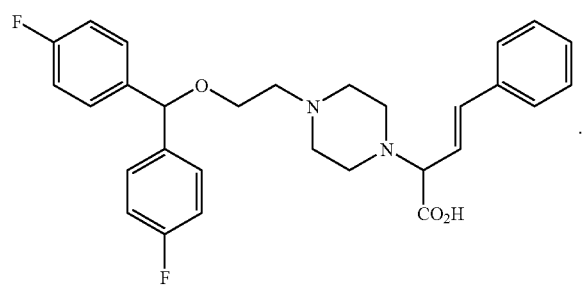
2. A polypharmacophore selected from the group consisting of:
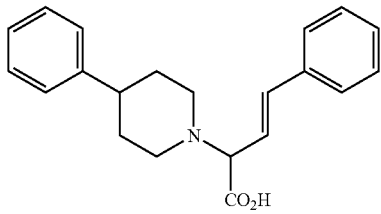
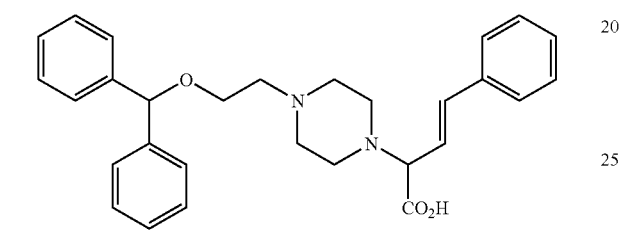
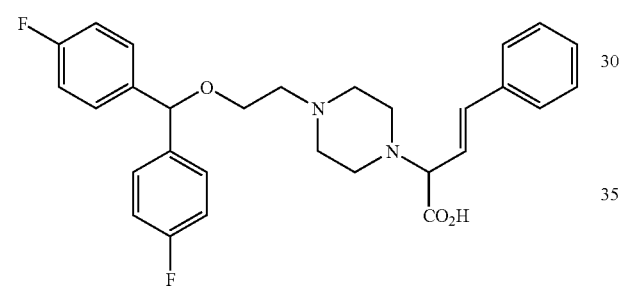
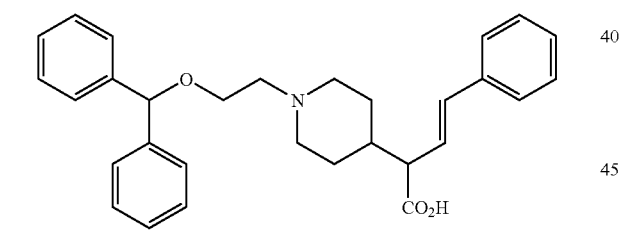
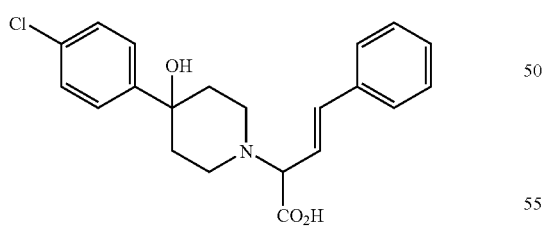
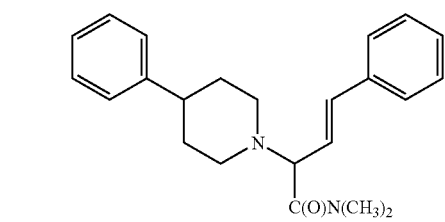
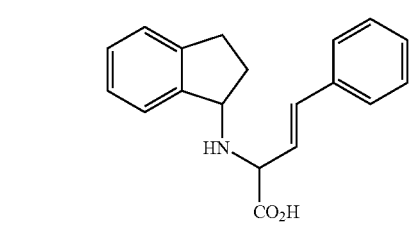
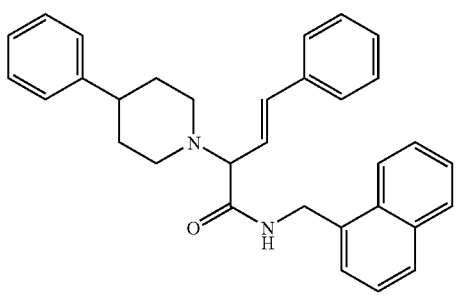
and
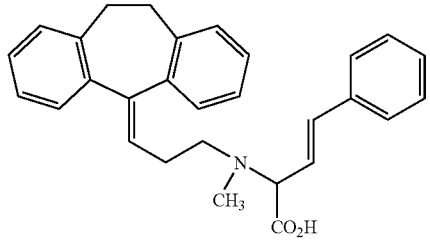
3. A pharmaceutical composition comprising a polypharmacophore of claims 1 or 2, or a pharmaceutically acceptable salt thereof, and a pharmaceutically acceptable diluent or carrier.
* * * * *